(12) United States Patent
Singh et al.

(10) Patent No.: US 11,103,207 B1
(45) Date of Patent: Aug. 31, 2021

(54) DOUBLE-PULSED X-RAY SOURCE AND APPLICATIONS

(71) Applicant: Radiation Monitoring Devices, Inc., Watertown, MA (US)

(72) Inventors: Bipin Singh, Watertown, MA (US); Vivek V. Nagarkar, Watertown, MA (US)

(73) Assignee: Radiation Monitorng Devices, Inc., Watertown, MA (US)

(*) Notice: Subject to any disclaimer, the term of this patent is extended or adjusted under 35 U.S.C. 154(b) by 0 days.

(21) Appl. No.: 16/235,388

(22) Filed: Dec. 28, 2018

Related U.S. Application Data

(60) Provisional application No. 62/611,145, filed on Dec. 28, 2017, provisional application No. 62/611,691, filed on Dec. 29, 2017.

(51) Int. Cl.
*A61B 6/00* (2006.01)
*H05G 1/20* (2006.01)
*H05G 1/22* (2006.01)
*H01J 35/02* (2006.01)

(52) U.S. Cl.
CPC ............... *A61B 6/504* (2013.01); *A61B 6/40* (2013.01); *A61B 6/4233* (2013.01); *A61B 6/468* (2013.01); *A61B 6/484* (2013.01); *A61B 6/487* (2013.01); *H01J 35/025* (2013.01); *H05G 1/20* (2013.01); *H05G 1/22* (2013.01)

(58) Field of Classification Search
CPC ....... A61B 6/40; A61B 6/4007; A61B 6/4014; A61B 6/42; A61B 6/4208; A61B 6/4216; A61B 6/4233; A61B 6/4266; A61B 6/44; A61B 6/4452; A61B 6/481; A61B 6/484; A61B 6/486; A61B 6/487; A61B 6/504; A61B 6/507; G01N 23/04; G01N 23/043; G01N 23/06; G01N 23/083; G01N 23/087; G01N 23/10; G01N 23/12; G01N 23/16; G01N 23/18; H01J 35/02; H01J 35/025; H05G 1/20; H05G 1/22
USPC .................... 378/51–59, 62, 101, 106, 98.12
See application file for complete search history.

(56) References Cited

U.S. PATENT DOCUMENTS

| | | | |
|---|---|---|---|
| 3,719,846 A | 3/1973 | Berends et al. | |
| 4,117,334 A * | 9/1978 | Strauts | H05G 1/06 378/102 |
| 4,184,075 A * | 1/1980 | Ebersberger | H02M 7/523 363/142 |

(Continued)

OTHER PUBLICATIONS

C. Michail et al., "Measurement of the luminescence properties of Gd2O2S: Pr,Ce,F powder scintillators under X-ray radiation," Radiation Measurements 70 (2014) 59-64.*

(Continued)

*Primary Examiner* — Allen C. Ho
(74) *Attorney, Agent, or Firm* — Culhane Meadows PLLC; Orlando Lopez

(57) ABSTRACT

Systems that can overcome the limitations of current blood flow measurement systems and systems that can track in 3D the explosively driven fragments traveling at 1,000 m/s or faster, will provide temporal resolution of 1 μs, spatial resolution of 50 μm to 1 mm (or finer based on geometry), and allow imaging over at least 122×122 cm² area are disclosed hereinbelow. These systems use a double-pulsed X-ray generator.

18 Claims, 12 Drawing Sheets

(56) References Cited

U.S. PATENT DOCUMENTS

| | | | | |
|---|---|---|---|---|
| 4,514,795 | A * | 4/1985 | van der Zwart | H05G 1/10 363/139 |
| 4,517,472 | A | 5/1985 | Ruitbert et al. | |
| 4,653,082 | A * | 3/1987 | Tsuchiya | H05G 1/32 363/28 |
| 4,661,896 | A * | 4/1987 | Kobayashi | H05G 1/20 323/266 |
| 4,700,372 | A * | 10/1987 | Tsuchiya | H05G 1/32 363/138 |
| 4,710,860 | A * | 12/1987 | Tsuchiya | H05G 1/32 363/28 |
| 4,725,938 | A * | 2/1988 | Onodera | H02M 3/135 363/28 |
| 4,742,535 | A * | 5/1988 | Hino | H05G 1/46 323/222 |
| 4,797,908 | A * | 1/1989 | Tanaka | H05G 1/20 363/28 |
| 5,060,252 | A * | 10/1991 | Vogler | H05G 1/66 378/101 |
| 5,077,771 | A * | 12/1991 | Skillicorn | H01J 35/16 378/102 |
| 5,121,317 | A * | 6/1992 | Vogler | H05G 1/20 363/136 |
| 5,200,645 | A * | 4/1993 | Laeuffer | H05G 1/10 307/82 |
| 5,267,138 | A * | 11/1993 | Shores | H02M 3/3376 363/132 |
| 5,391,879 | A * | 2/1995 | Tran | G01T 1/2018 250/367 |
| 5,586,017 | A * | 12/1996 | Rohrbeck | H02P 25/032 363/39 |
| 5,648,997 | A * | 7/1997 | Chao | A61B 6/06 378/147 |
| 5,731,968 | A * | 3/1998 | Van Der Broeck | H05G 1/20 363/17 |
| 6,072,856 | A * | 6/2000 | Van Der Broeck | H02M 3/337 363/132 |
| 6,128,367 | A | 10/2000 | Foerst et al. | |
| 6,134,300 | A | 10/2000 | Trebes et al. | |
| 7,180,068 | B1 * | 2/2007 | Brecher | C09K 11/772 250/361 R |
| 7,327,827 | B2 * | 2/2008 | Sakamoto | H05G 1/12 378/101 |
| 7,759,645 | B1 * | 7/2010 | Brecher | G01T 1/202 250/361 R |
| 8,755,491 | B2 * | 6/2014 | Rosevear | H05G 1/12 378/103 |
| 8,761,344 | B2 | 6/2014 | Reynolds et al. | |
| 8,908,826 | B2 * | 12/2014 | Bernhardt | A61B 6/022 378/42 |
| 10,470,731 | B2 * | 11/2019 | Rauch | A61B 6/541 |
| 2017/0295634 | A1 * | 10/2017 | Garcia Tormo | H05G 1/12 |

OTHER PUBLICATIONS

Hanwook Park, Eunseop Yeom & Sang Joon Lee, "X-ray PIV measurement of blood flow in deep vessels of a rat: An in vivo feasibility study", Scientific Reports, 6:19194, (2016).

Hanwook Park, Eunseop Yeom, Seung-Jun Seo, Jae-Hong Lim & Sang-Joon Lee, "Measurement of real pulsatile blood flow using X-ray PIV technique with CO2 microbubbles", Scientific Reports, 5 : 8840, (2015).

T. Miyoshi, T. Tominari, M. Hayashi, A. Ito, M. Yoshinaga, S. Ueno, T. Oshima, and S. Wada, "300 V Field-MOS FETs for HV-Switching", Proceedings of the 23rd International Symposium on Power Semiconductor Devices & IC's May 23-26, (2011).

\* cited by examiner

DOUBLE-PULSED X-RAY SOURCE AND APPLICATIONS

STATEMENT REGARDING RELATED APPLICATIONS

This application claims priority to U.S. Provisional Patent Application No. 62/611,145, filed on Dec. 28, 2017, entitled DOUBLE-PULSED X-RAY SOURCE AND APPLICATIONS, and U.S. Provisional Patent Application No. 62/611,691 filed on Dec. 29, 2017, entitled DOUBLE-PULSED X-RAY SOURCE AND APPLICATIONS, which are incorporated by reference herein in their entirety for all purposes.

STATEMENT REGARDING FEDERALLY SPONSORED RESEARCH OR DEVELOPMENT

This invention was made with U.S. Government support from the National Institutes of Health (NIH) under grant R43 HL132664-01 and from the Department of Defense (DOD) under grant FA9550-17-P-0003 DEF. The U.S. Government has certain rights in the invention.

BACKGROUND

This invention relates generally to double-pulsed X-ray source with high enough fluence to provide a good SNR of at least 10:1, applications of the double-pulsed X-ray source.

Diseases in the vascular system are still the leading cause of mortality and morbidity in developed countries despite considerable therapeutic progress in recent years. For the risk assessment of atherothrombosis, aneurysms, currently the most widely accepted indicators are still maximum diameter and expansion rate. Many studies have shown that configuration-based determinant of plaque rupture and aneurysm rupture is not reliable. Other risk factors, for example, hypertension and smoking, only offer general recommendations and are not usually a justification for surgery. Clearly, a more accurate indicator is needed in order to reduce the incidence of rupture. Other indicators, such as wall shear stress (WSS), mean velocity amplitude, and mechanical wall stress have been suggested by different research groups as indicators for diagnosis of vascular disease, treatment planning and risk assessment. These quantities are all coherently correlated for most cases. There is a critical need for reliable correlations between hemodynamics and vascular diseases, and accurate assessment of treatments.

Driven by the flow shear-mediated initiation hypothesis, many studies have shown that there is a correlation between very low shear stresses and the loss of permeability of the endothelial cell membrane, while some researchers argue that high WSS is the cause of rupture of aneurysms. WSS is not measurable from a direct measurement; nevertheless, it can be derived from the velocity distribution near the wall. Therefore, accurate and detailed flow velocity distribution plays the key role in estimating WSS. Approaches for instantaneous in vivo flow measurement include ultrasonography, particle image velocimetry (NV), MRI and X-ray imaging. However, no one method is optimal for meeting the clinical requirements for recovering precise velocities and WSS. Ultrasound imaging is inexpensive, portable, and widely available, but this modality has a number of limitations including low spatial resolution, and limited penetration depth. PIV is capable of accurately measuring instantaneous velocity fields that have a high dynamic range, but suffer from the limited optical access and seeding challenge. MRI is useful for aneurysms of large size (>3~5 mm), however, MM suffers from low temporal and spatial resolution, and is restricted to patients with MRI-compatible treatment device. Intra-arterial catheter angiography continues to be the "gold standard" in the diagnostic evaluation of intracranial aneurysms. Transcatheter studies provide the most information about small perforating vessels and produce higher-resolution images than other imaging modalities. The current techniques cannot satisfy the requirement of high-resolution, high accuracy measurement of blood velocities, therefore techniques for precise and reliable measurement of instantaneous blood velocity in a minimally invasive manner are critically needed.

The best approach to measuring blood flow velocity and the associated mechanical stresses is to introduce gold micro-particles into the blood stream and track individual particles using a high spatial and temporal resolution X-ray imager. Unfortunately, the technology needed to track individual micro-particles flowing in vivo at speeds in excess of 1 m/s does not exist.

Optical flow-type algorithms are the only ones fully capable of producing 2D flow maps, and are well extendable to 3D imaging such as rotational X-ray angiography. However, traditional OFM suffers from low frame rate and vulnerability to diffusion; thus, the accuracy and reliability of OFM cannot satisfy the clinical requirement. Despite several methods developed to address this need, none of the current methods are fully validated for the assessment of detailed 2D velocity field and WSS. The major problem in applying the OFM to physical fluid/blood measurement is that the correlation between the OFM and fluid flow has not been established quantitatively.

In another field, methods currently used to characterize ballistic impacts and detonations of warheads are limited by their poor temporal resolution, inability to provide measurements in environments with high luminosity fireballs or with significant debris, and inability to map the trajectories of fragments traveling at high speeds of few km/s. Several techniques have been used to determine the velocity profile and characterize the fragment trajectory with varying degrees of success. For example, Particle Image Velocimetry (PIV) has been used to measure the velocity of an explosively driven expanding cloud of particles, whereas Particle Doppler Velocimetry (PDV) has been used to measure velocity during high-speed tests. Schlieren imaging has also been demonstrated for high-speed imaging.

However, one of the challenges in imaging explosively driven fragments is to image through opaque fireballs, which renders optical techniques ineffective in imaging early time events even though optical imaging techniques are capable of providing high-speed imaging data with high resolution. On the other hand, radio waves, particularly radar techniques, can see through the fireball, but due to the long wavelengths used, they lack the resolution to discriminate objects ~1 $cm^3$ in size. Techniques such as terahertz (THz) imaging can penetrate through the fireball and also provide high resolution. However, with the current state-of-the-art THz sources and detectors, THz imaging currently is incapable of imaging 1 $cm^3$ or smaller fragments traveling at 1,000 m/s or higher There is a need for systems that can overcome the limitations of current blood flow measurement systems It is a further need for systems that can track in 3D the explosively driven fragments traveling at 1,000 m/s or faster, will provide temporal resolution of spatial resolution of 50

µm to 1 mm (or finer based on geometry), and allow imaging over at least 122×122 cm² area.

BRIEF SUMMARY

Systems that can overcome the limitations of current blood flow measurement systems and systems that can track in 3D the explosively driven fragments traveling at 1,000 m/s or faster, will provide temporal resolution of spatial resolution of 50 µm to 1 mm (or finer based on geometry), and allow imaging over at least 122×122 cm² area are disclosed hereinbelow. These systems use a double-pulsed X-ray generator of these teachings.

In one or more embodiments, the double pulsed x-ray source of these teachings includes a high-voltage source having a plurality of circuits, each circuit from the plurality of circuits, including a two terminal input port, a DC voltage source of predetermined voltage connected between a first terminal of the input port and a second terminal of the two terminal input port, the first terminal of the two terminal input port being connected to a positive voltage terminal of the DC voltage source and the second terminal of the two terminal input port being connected to a ground terminal of the DC voltage source, a first high-voltage switch connected to the first terminal of the two terminal input port, a second high-voltage switch connected between an output terminal of the first high-voltage switch and the second terminal of the two terminal input port, a first capacitor, a transformer having a predetermined turn ratio, the first capacitor being connected between an output terminal of the first high-voltage switch and a first terminal of a primary winding of the transformer, a second terminal of the primary winding of the transformer being connected to the second terminal of the two terminal input port, the first capacitor and a leakage inductance of the transformer constitute a resonant circuit, a second capacitor connected from a first terminal of the secondary winding of the transformer to a second terminal of the secondary winding of the transformer, and, a resistor connected in parallel with the second capacitor; the second capacitor and the resistor configured to extinguish output in a predetermined time. The double pulsed x-ray source of these teachings also includes a controller unit operatively connected to the first high-voltage switch and the second high-voltage switch. In said each circuit; the controller unit configured to provide pulses, which, when provided to an x-ray tube, result in the double pulsed x-ray source. In a first circuit from the plurality of circuits, the first terminal of the secondary winding is connected to the second terminal of the secondary winding of a subsequent circuit from the plurality of circuits; in every subsequent circuit from the plurality of circuits except for a last circuit from the plurality of circuits, the first terminal of the secondary winding is connected to the second terminal of the secondary winding of a subsequent circuit from the plurality of circuits and the second terminal of the secondary winding is connected to the first terminal of the secondary winding in a preceding circuit from the plurality of circuits; in the last circuit from the plurality of circuits, the second terminal of the secondary winding is connected to the first terminal of the secondary winding of a preceding circuit from the plurality of circuits.

In one instance, each circuit from the plurality of circuit includes a diode connected between the first terminal of the secondary winding of the transformer and the second capacitor, the second capacitor being connected between an output terminal of the diode and the second terminal of the secondary winding of the transformer; in the first circuit from the plurality of circuits, the second terminal of the secondary winding is connected to ground and an anode terminal of an x-ray tube is connected to the second terminal of the secondary winding in the transformer of the first circuit; in the last circuit from the plurality of circuits, the output terminal of the diode is also connected to a cathode terminal of the x-ray tube; the controller unit is also operatively connected to a filament control unit for the x-ray tube and to a current sensor sensing current to the anode terminal of the x-ray tube; the controller unit being configured to control pulse width, tube currents and voltages.

In another instance, the double pulsed x-ray source also includes a bipolar x-ray tube receiving a voltage between the second terminal of the secondary winding of the first circuit from the plurality of circuits and the output terminal of the diode of the last circuit from the plurality of circuits.

In one or more embodiments, the imaging system of these teachings includes the double pulsed x-ray source of these teachings configured to illuminate a flowing fluid, a scintillator configured to receive x-rays from the double pulsed x-ray source after illuminating the flowing fluid, a detector, and an optical unit configured to deliver output from the scintillator to the detector.

In one or more embodiments, the method for fluid flow measurements of these teachings includes illuminating a section of fluid flow with at least one double pulsed x-ray source, where wo pulses in the double pulsed x-ray source are separated by between 25 µs and 100 µs, receiving x-rays from the double pulsed x-ray source after illuminating and propagating through the flowing fluid at one or more scintillators, providing output of the one or more scintillators to one or more detectors, output from the one or more detectors being used to obtain preselected fluid and fluid flow characteristics.

Other embodiments are also disclosed herein below.

For a better understanding of the present teachings, together with other and further objects thereof, reference is made to the accompanying drawings and detailed description and its scope is pointed out in the appended claims.

DETAILED DESCRIPTION

Systems that can overcome the limitations of current blood flow measurement systems and systems that can track in 3D the explosively driven fragments traveling at 1,000 m/s or faster, will provide temporal resolution of 1 µs, spatial resolution of 50 µm to 1 mm (or finer based on geometry), and allow imaging over at least 122×122 cm$^2$ area are disclosed hereinbelow. These systems use a double-pulsed X-ray generator of these teachings.

A "tapered optical fiber," also called a fiber optic taper, as used here in, is an optical fiber which are over some length stretched out to a smaller diameter.

A "turns ratio" of a transformer, as used herein, refers to the number of turns of the primary coil divided by the number of turns of the secondary coil.

The double pulsed X-ray source of these teachings is a repeatable, double-pulsed X-ray source with high enough fluence to provide a good SNR of at least 10:1. This will allow the adoption of optical PIV techniques for the volumetric X-ray imaging. Most laboratory continuous X-ray sources produce at the most $10^8$ X-rays/mm$^2$/s, which means that in a 50 ns pulse duration, only 5 X-rays/mm$^2$ are produced.

Figure 1:
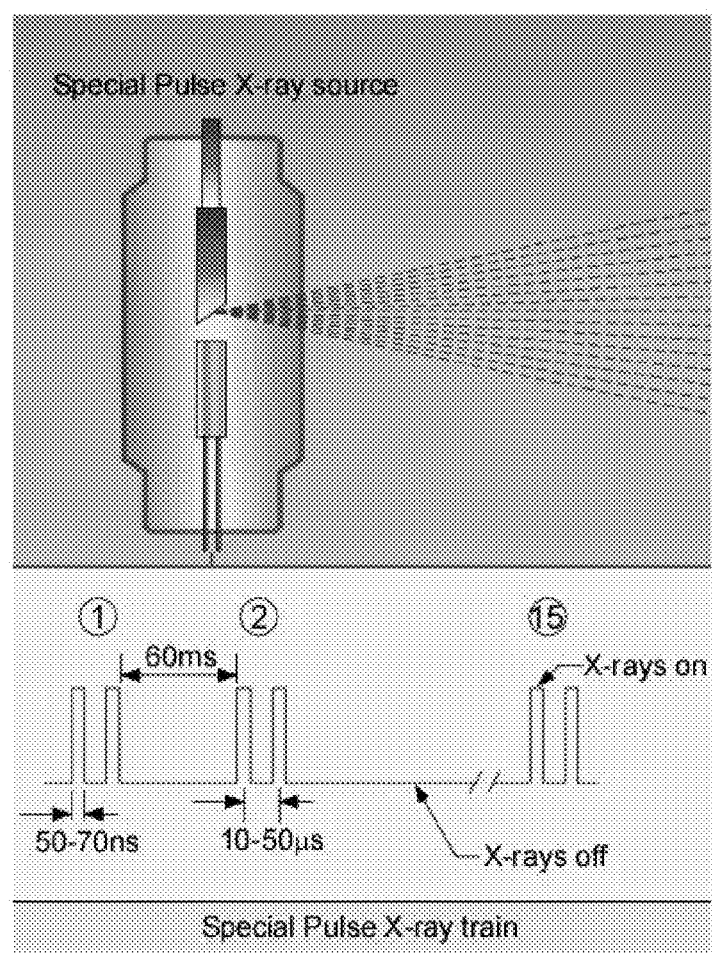
FIG. 1 shows the design the X-ray source of these teachings and its characteristics.

The design the X-ray source of these teachings has characteristics illustrated in FIG. 1.

FIG. 1 shows a schematic of one embodiment the X-ray source, with the inset below showing the pulse train to be produced by the special double-pulse X-ray source that is developed during the program. Each individual X-ray pulse is 50-70 ns in duration, and the two pulses are separated by 10-50 µs interval. 15 such double pulses (with ~60 ms interval between them) is produced per second.

The system has the capability to generate and detect two X-ray pulses with sub-microsecond separation.

In one or more embodiments, the imaging system of these teachings includes the double pulsed x-ray source of these teachings configured to illuminate a flowing fluid, a scintillator configured to receive x-rays from the double pulsed x-ray source after illuminating the flowing fluid, a detector, and an optical unit configured to deliver output from the scintillator to the detector.

In one further embodiment, the optical unit includes a fiber-optic faceplate receiving the output from the microcolumnar, low afterglow scintillator, and, a fiberoptic taper optically operatively connected to the fiber-optic faceplate and configured to deliver the output from the scintillator to the detector; the detector being in a pixelated detector. Embodiments without the fiber-optic faceplate are also within the scope of these teachings.

In one instance, the scintillator is a micro-columnar, low afterglow scintillator, and the micro-columnar, low afterglow scintillator comprises a CsI:Tl, Sm co-doped film. In another instance, two pulses in the double pulsed x-ray source are separated by between 25 µs and 100 µs. The uncertainty in the time delay between the first and second pulses is estimated to be less than about 0.6 µs.

In a further instance, the scintillator comprises $Gd_2O_2S$ (Pr). In still another instance, the detector is a pixelated detector.

Blood Flow Measurements

Specifically, clinicians benefit from perioperative blood velocity measurements for diagnosis, treatment planning and treatment assessment, since the method will not re-quire movement of the patient, nor any additional procedures. The velocity measurement happens when the routine DSA is processed. This advantage will make technique very unique and beneficial to both patients and physicians. Computational fluid dynamics (CFD) researchers lack reliable in vivo flow data for validation, which creates barriers preventing broad applications of CFD on hemodynamics, and will also benefit from this. To enable this new technique and overcome the limitations of current blood flow measurement systems, we develop a novel ultrafast X-ray imaging system incorporating a bright, fast, afterglow-free microcolumnar scintillator film, and a double-pulsed X-ray generator. The schematic of the system for Blood Flow Measurements is shown in FIG. 1a.

Figure 1A:
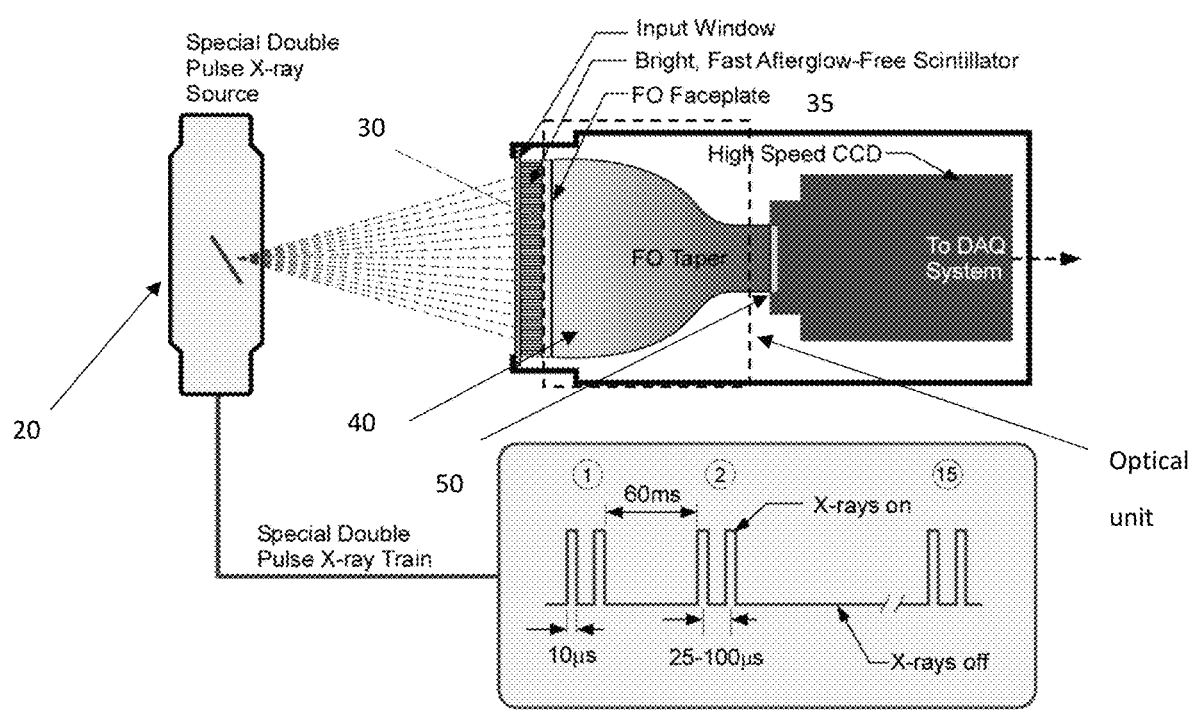
FIG. 1a shows schematic of the system for Blood Flow Measurements.

FIG. 1a shows a schematic of one embodiment of the imaging system showing a double pulsed X-ray source 20, image intensifier, fiberoptic taper, and ultrafast imaging sensor. The inset below shows the pulse train to be produced by the special double-pulse X-ray source. Each individual X-ray pulse is 50-70 ns in duration, and the two pulses are separated by 10-50 µs interval. 15 such double pulses (with ~60 ms interval between them) is produced within each cardiac cycle.

Referring to FIG. 1a, in the embodiment shown therein, a double pulsed x-ray source 20 of these teachings provides x-rays that illuminate and propagate through flow of interest. After propagating through a region of interest, the x-rays are received by a scintillator 30. The scintillator 30 converts the x-rays to light (different wavelengths photons). An optical unit, a fiber-optic faceplate 35 and a fiber optic taper 40 in the embodiment shown, delivers the light to a detector 50. In the embodiment shown, the detector 50 is a CCD. It should be noted that other detector also within the scope of these teachings. The embodiment shown in FIG. 1A is an embodiment that could be used for blood flow measurements.

An exemplary embodiment is presented herein below. It should be noted that these teachings are not limited to the exemplary embodiment.

The imaging system includes a high-performance, microcolumnar film of a co-doped CsI:Tl,Sm scintillator (see Ovechkina E. E., S. R. Miller, V. Gaysinskiy, C. Brecher, V. V. Nagarkar, Effect of Tl$^+$ and Sm$^{2+}$ Concentrations on Afterglow Suppression in CsI:Tl,Sm Crystals, *IEEE Trans. Nucl. Sci.*, vol. 59, no. 5, pp 2095-2097, 2012, Nagarkar V V, Gaysinskiy V, Ovechkina E E, Miller S R, Brecher C, Lempicki A, and Bartram R H, "Scintillation properties and applications of reduced-afterglow co-doped CsI:Tl", *Proc. SPIE* 6707, 67070D (2007), Nagarkar V V, Gaysinskiy V, Ovechkina E E, Miller S R, Cool S, Thacker S, Brecher C, and Lempicki A, "Suppression of afterglow and hysteresis in CsI:Tl by codoping with Sm$^{2+}$: Fabrication of microcolumnar films for high-resolution high-speed imaging," Presented at *IEEE NSS/MIC* 2007, Hawaii, October 2007, V. Nagarkar et. Al., "Scintillator Materials with Reduced Afterglow and Method of Preparation," U.S. Pat. No. 7,180,068, Feb. 22, 2007, C. Brecher, V. Nagarkar, "Scintillation materials with reduced afterglow and method of preparation," U.S. Pat. No. 7,759,645, Issue Date Jul. 20, 2010, all of which are incorporated by reference herein in their entirety and for all purposes) coupled to a pixelated detector via a 2:1 fiberoptic (FO) taper. In some embodiments, in order to maximize the SNR for single photon imaging, a 40 mm diameter single stage MCP140 image intensifier (such as that from Photek (East Sussex, UK)) is used to couple the scintillator to the fiberoptic taper. In other embodiments, the image intensifier is not necessary. A schematic diagram of one embodiment of the imaging system is shown in FIG. 1a., the system shown there in, includes a low-cost detector, a bright, afterglow-free microcolumnar CsI:Tl,Sm codoped scintillator film, and a double-pulsed X-ray source In one embodiment, the detector 50 consists of a high-performance, microcolumnar film of co-doped CsI:Tl,Sm scintillator coupled to a customized high frame rate pco.pixelfly CCD camera from PCO-Tech (Romulus, Mich.) via a 4.6:1 fiber optic (FO) taper 40 in order to maximize the SNR for single photon imaging. The 4.6:1 demagnifying fiber optic (FO) taper 40 provides an imaging area of 4 cm×4 cm. The pco pixelfly camera has a pixel resolution of 1392× 1040, each 6.45×6.45 μm² in size, and provides megapixel resolution with 14-bit pixel depth (ADC). It has a low readout noise of 6e⁻. Because of its extremely short interframe time of 1 μs, it can be double pulsed and its operation can be synchronized with that of the double pulsed X-ray source 20. Thus, it is perfectly suited for the proposed blood flow velocimetry application. An important feature of the detector 50 is that it can operate at any frame rate without binning, thereby preserving the intrinsic spatial resolution at all speeds. Furthermore, the incorporation of the fiber optic (FO) taper 40 allows the detection of 30 keV X-ray photons in a 10 μs pulse with a SNR of 21:1, as described herein below. Therefore, there is no need to use an image intensifier, as was originally envisioned. Eliminating the image intensifier preserves the dynamic range of the detector 50, and also significantly reduces the system cost. Design of a cost-effective system was one of the goals of the Phase I research, and it has been successfully accomplished.

As can be seen-Table 1, each 25×25 μm pixel will receive 1950 X-rays per 10 μs pulse. This is a large enough number and even after considering X-ray attenuation in the mass surrounding the artery a few tens of X-rays/pixel/pulse can be anticipated. The key benefit of this is that the detector 50 need not be designed for a single X-ray sensitivity as the detector 50 will be integrating the signal over the entire duration of the pulse. Noteworthy advantage of the signal integration is that the SNR in the detector 50 will be high enough to eliminate the need for an expensive image intensifier from the design, With the estimated blood velocity of ~1 m/s, the gold micro-particles will travel on an average 1 μm per us or a total distance of 10 μm during the 10 μs X-ray pulse. The distance traveled being less than the anticipated spatial resolution of 25 μm at the detector input, integrating the detector signal for 10 μs will not cause any significant image blur. What this implies is that the detector frame rate does not have to be on the order of 1 Mfps. Depending on duration between consecutive pulses it can be lower by a factor of 10 or higher. Both of these aforementioned advantages translate into simplified system design and significantly reduced detector costs.

In one exemplary embodiment, a commercially available low-cost detector that is suitable for the described application, provided its sensitivity can be enhanced by an order of magnitude or so. The detector 50 of our choice is PCO Pixelfly USB from PCO-Tech, which is a high performance digital 14-bit CCD camera system that features state-of-the-art in CCD and electronics technology. The PCO Pixelfly USB CCD has a high quantum efficiency (>60% in green), high dynamic range (>14 bits), and very low readout noise (~6 e−/pixel/sec for 24 MHz readout rate). Available exposure times range from microseconds to a minute and the camera can capture up to 13.5 fps at full resolution or 27 fps with 2× vertical binning. The detailed key specifications of the camera are outlined in Table 2.

TABLE 1

Calculations for X-rays produced by the X-ray tube.

| Parameter | Value |
|---|---|
| Anode current | 1 mA |
| Tube cone angle | 30° |
| Total 80kVp X-rays/30° Solid angle/second | $6.25 \times 10^{15}$ |

TABLE 1-continued

Calculations for X-rays produced by the X-ray tube.

| Parameter | Value |
|---|---|
| Anticipated Source to detector distance | 30 cm |
| Anticipated X-ray detector active area | 4 × 4 cm² |
| Fraction of X-rays impinging on the detector | 0.08 |
| Number of X-rays on the detector per second | $5 \times 10^{14}$ |
| Effective pixel size on the detector | 25 × 25 μm² |
| Number of X-rays per pixel per second | $1.95 \times 10^8$ |
| Number of X-rays per pixel per microsecond | $1.95 \times 10^2$ |
| Number of X-rays per pixel per 10 microseconds | 1950 |

TABLE 2

Specifications of the Pixelfly CCD camera.

| Parameter | Specifications |
|---|---|
| Image sensor | ICX285AL |
| Resolution (h × v) | 1392 × 1040 pixel (normal) |
| Pixel size (h × v) | 6.45 μm × 6.45 μm |
| MTF | 77.5 lp/mm (theoretical) |
| Full well capacity | 16 000 e, 24000 e (binned mode) |
| Readout noise | 5 e⁻ rms @ 12 MHz (typ.), 6-8 e⁻ @ 24 MHz |
| Dynamic range | 2667:1 (68 dB), 4000:1 (72 dB, binning) |
| Quantum efficiency | 62% @ peak |
| Spectral range | 290 nm to 1100 nm |
| Dark current | 1 e-/pixel/s @ 23° C. |
| Max. frame rate | 13.5 fps |
| Exposure/shutter time | 1 μs to 60 s |
| Dynamic range | A/D 14 bit |
| Pixel scan rate | 12 MHz/24 MHz |
| Pixel data rate | 19.5 Mpixel/s |
| Binning (hor × ver) | 1 × 1 to 4 × 4 |
| Interframing time | 3 1 μs |
| Data interface | USB 2.0 |

In its commercial configuration, the camera is lens coupled. While adequate for some applications, lens coupling is inefficient and causes reduced sensitivity because the lens is a major quantum sink. Higher sensitivity needed for our application will be achieved by eliminating the lens coupling and replacing it with a custom fiberoptic coupling. We use a fiberoptic reducer rather than the 1:1 plug, which also allows enhancing the active imaging area of the detector. In order to enhance the active image area to ~4×4 cm², ~4.6:1 fiberoptic taper 40 will be optically bonded to the front of the CCD.

The overall mechanical assembly of the fiber optic taper 40 will be such that the large end of the fiber optic taper 40 will be slightly elevated from the rest of the hardware to allow easy access and ease of mounting of a scintillator 30. With fiberoptic in place the camera sensitivity is expected to be substantially boosted. A detailed calculation of the SNR in the system for a 10 μs X-ray pulse is outlined in Table 3. It is assumed that 90% of incident X-rays are absorbed in the mass surrounding the artery, therefore only 10% incident X-rays (195 X-rays) are taken into account for the SNR calculations. For a comparison, sensitivity of lens coupled system is also included. One shortcoming of the fiber optic taper 40 is that the effective pixel size will increase from 6 μm at the CCD to ~24 μm at the large end of the fiberoptic. However, this loss in resolution can be well compensated by adjusting magnification in the image.

TABLE 3

SNR estimation for the Phase II system for FO and lens coupling.

| Parameter | Fiberoptic coupling | Lens coupling |
|---|---|---|
| PCO Pixelfly USB CCD Size (mm × mm) | 9 × 7 | 9 × 7 |
| Fiberoptic Taper Ratio | 4.6 | |
| Active Area with FO Taper (Length mm) | 40 | 40 |
| Active Area with FO Taper (Width mm) | 30 | 30 |
| CsI Light Output (Photons/MeV) | 52000 | 52000 |
| Incident Average X-Ray Energy (KeV) | 30 | 30 |
| Number of Incident X-Rays (for 90% Attenuation) | 195 | 195 |
| X-Ray absorption in 150 μm Thick CsI:Tl, Sm (%) | 65 | 65 |
| Screen Light Output | 197730 | 197730 |
| Light Towards the CCD (Optical Photons) | 138411 | 138411 |
| Taper/Lens Efficiency (%) | 5 | 0.1 |
| Light Photons Incident on CCD | 6990 | 138 |
| Detector Intrinsic pixel size (um) | 29 | 29 |
| Signal Spread over Pixels | 9 | 9 |
| Signal Per Pixel (S) | 777 | 15 |
| CCD (QE) @ 540 nm (%) | 65 | 65 |
| Electrons generated at each pixel (S*QE) Smut | 505 | 10 |
| Excess Noise Factor (F) | 1 | 1 |
| Photon (Shot) Noise G*F*SQRT(S*QE) | 22 | 3 |
| Total Dark Related Signal (e-/pixel/frame) (D) | 1 | 1 |
| Dark Noise G*F*SQRT(D) | 1 | 1 |
| Read Noise e- rms (σR) | 7 | 7 |
| Total System Noise ($\sigma_{Total}$) | 24 | 8 |
| Signal to Noise ratio (SNR) $S_{Total}/\sigma_{Total}$ | 21 | 1 |

The scintillator 30 is an important component of the system. One embodiment of the imaging system is based on a 4 cm×4 cm film of a high-resolution, low-afterglow, bright microcolumnar CsI:Tl,Sm scintillator 30 coupled to a fiber optic (FO) taper 40, resulting in the higher sensitivity needed for blood flow velocimetry. Co-doped CsI:Tl,Sm is a newly developed scintillator 30 that reduces the afterglow and hysteresis associated with conventional CsI:Tl by several orders of magnitude (V. Nagarkar et. Al., "Scintillator Materials with Reduced Afterglow and Method of Preparation," U.S. Pat. No. 7,180,068, Feb. 22, 2007, C. Brecher, V. Nagarkar, "Scintillation materials with reduced afterglow and method of preparation," U.S. Pat. No. 7,759,645, Issue Date Jul. 20, 2010, all of which are incorporated by reference herein in their entirety and for all purposes) without sacrificing its excellent properties (light yield of over 60,000 Ph/MeV, rapid, 600 ns decay, high density of 4.5 gm/cc, high effective atomic number of 54, and a low cost of ~$250/kg) thereby making it a material well suited for high-speed, high-resolution imaging.

Microcolumnar films of co-doped CsI:Tl,Sm were fabricated by the evaporation of pre-synthesized materials from a single source. A premium was placed on maintaining the stoichiometry in the evaporated films and the concentration of the dopants. Various 2"×2" substrates were used to deposit microcolumnar co-doped CsI:Tl,Sm films with thickness ranging from 200-700 μm, which were suitable for imaging using hard X-rays. Factors such as substrate temperature and vapor deposition parameters determine the optical properties in the columnar film. Thus, these parameters were varied in a control manner to create stoichiometrically balanced microcolumnar structures.

Figures 2A, 2B:
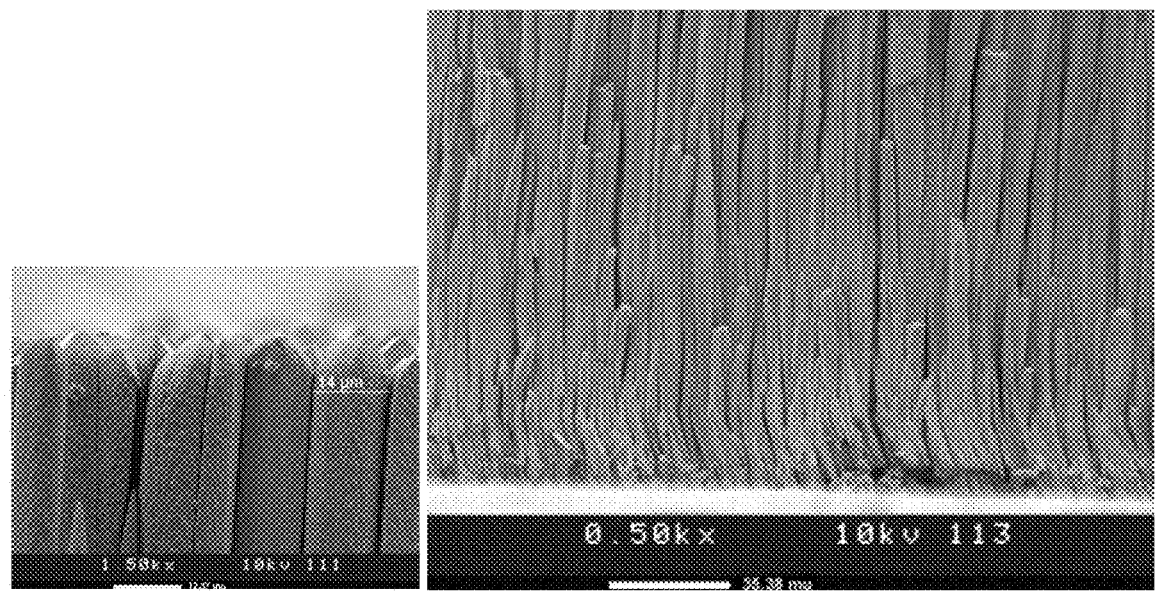
FIGS. 2a, 2b shows 700 µm thick $Sm^{2+}$ Co-doped CsI:Tl film grown using thermal vapor deposition.

The morphology of the fabricated films was characterized using SEM (see FIGS. 2a, 2b). FIGS. 2a and 2b shows 700 μm thick $Sm^{2+}$ Co-doped CsI:Tl film grown using thermal vapor deposition. (Left) SEM of the film top showing microcolumns in the range of 10 to 14 μm in diameter. The film retains its columnar structure all the way through its thickness. (Right) SEM of the same film showing substrate-film interface. The film growth initiates right from the bottom. With such excellent structure and high thickness co-doped CsI films simultaneously provide enhanced X-ray absorption, high spatial resolution, and afterglow free performance, making them the ideal choice for the imaging system of these teachings.

Figure 3:
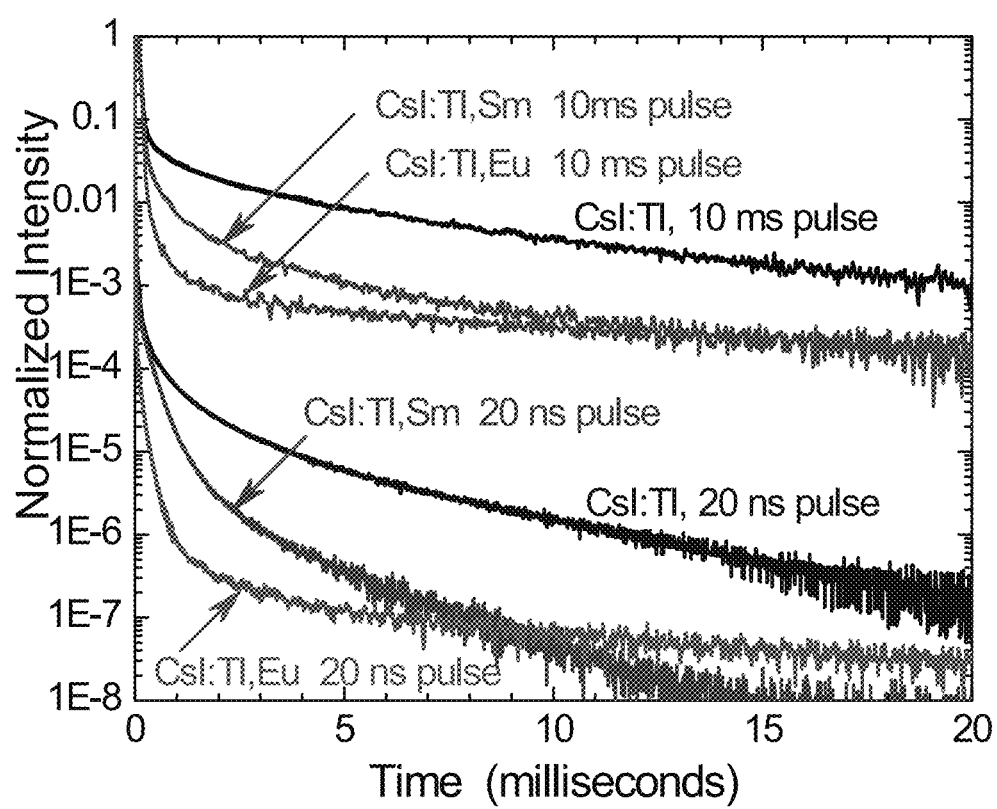
FIG. 3 shows decay traces of CsI:Tl with and without co-dopants, after excitation with long or short pulses.

The decay time and the afterglow of the films were also characterized, and are shown in FIG. 3. Imaging performance characteristics of the films were evaluated by measuring their light yield, spatial resolution in terms of modulation transfer function (MTF(f)), noise power spectrum NPS(f), and detective quantum efficiency DQE(f). Films exhibiting bright emission and high MTF were used for experiments.

To fabricate microcolumnar films of co-doped CsI:Tl,Sm, evaporation of the pre-synthesized materials from a single source is used, as this technique has shown the best results so far. A premium is placed on maintaining the stoichiometry in evaporated films and the concentration of various ions to optimal values determined based on our earlier crystal growth. Up to 200 μm thick films is initially fabricated for X-ray imaging tests, with thicknesses gradually increased with the aim of growing at least 600 μm thick films, suitable for hard X-ray (up to 140 kVp). These films are deposited on 7×7 cm2 graphite or other opaque substrates that are coated with a reflective material prior to deposition, and will match the area of the detector (Table 4) to be used during evaluations. Systems needed to accomplish such growth are readily available and in regular use at RMD. Factors such as substrate temperature and vapor deposition parameters determine the optical properties in the columnar film. Thus, these parameters are varied in a control manner to create stoichiometrically balanced microcolumnar structures. Fabricated films undergo SEM characterization for morphology evaluation. Imaging performance characteristics of the films are evaluated by measuring their light yield, spatial resolution in terms of modulation transfer function (MTF(f)), noise power spectrum NPS(f), and detective quantum efficiency DQE(f). Films that show bright emission and high MTF, on the order of 10-12 lp/mm (with 10% modulation), is used.

TABLE 4

Specifications of the initial detector.

| Parameter | Specifications |
|---|---|
| Image Area | 7 cm × 7 cm |
| Effective pixel size with 3.78:1 FO taper | 64 μm × 64 μm |
| Sensor pixel resolution | 1024 × 1024 |
| Frame rate at full pixel resolution | 2,000 fps |
| Maximum frame rate | 120,000 fps |
| Sensitivity for 100 keV photons | >95% |
| SNR for 100 keV photon (gain = 100) | 8.8 |

TABLE 5

Frame rate pixel resolution

| Frame Rate (fps) | Pixel Resolution (H × V) | FOV (H × V) mm² |
|---|---|---|
| 2,000 | 1024 × 1024 | 70 × 70 |
| 4,000 | 1024 × 512 | 70 × 35 |
| 10,000 | 512 × 256 | 35 × 18 |
| 24,000 | 512 × 128 | 35 × 9 |
| 50,000 | 256 × 64 | 18 × 4 |

TABLE 5-continued

Frame rate pixel resolution

| Frame Rate (fps) | Pixel Resolution (H × V) | FOV (H × V) mm² |
|---|---|---|
| 100,000 | 128 × 32 | 9 × 2 |
| 120,000 | 128 × 16 | 9 × 1 |

Currently there is no commercially available X-ray source that can satisfy the needs of the proposed application. In particular, what is required is a double-pulsed X-ray source 20 with high enough fluence to provide a good SNR of at least 10:1. Moreover, the double-pulsed X-ray source 20 should be capable of producing a train of around 15 double pulses per second. Most laboratory X-ray sources produce $10^8$ X-rays/mm²/s, however none of the sources on the market are capable of producing desired microsecond X-ray pulses.

In one or more embodiments, the double pulsed x-ray source 20 of these teachings includes a high-voltage source having a plurality of circuits, each circuit from the plurality of circuits, including a two terminal input port, a DC voltage source of predetermined voltage connected between a first terminal of the input port and a second terminal of the two terminal input port, the first terminal of the two terminal input port being connected to a positive voltage terminal of the DC voltage source and the second terminal of the two terminal input port being connected to a ground terminal of the DC voltage source, a first high-voltage switch connected to the first terminal of the two terminal input port, a second high-voltage switch connected between an output terminal of the first high-voltage switch and the second terminal of the two terminal input port, a first capacitor, a transformer having a predetermined turn ratio, the first capacitor being connected between an output terminal of the first high-voltage switch and a first terminal of a primary winding of the transformer, a second terminal of the primary winding of the transformer being connected to the second terminal of the two terminal input port, the first capacitor and a leakage inductance of the transformer constitute a resonant circuit, a second capacitor connected from a first terminal of the secondary winding of the transformer to a second terminal of the secondary winding of the transformer, and, a resistor connected in parallel with the second capacitor; the second capacitor and the resistor configured to extinguish output in a predetermined time. The double pulsed x-ray source 20 of these teachings also includes a controller unit operatively connected to the first high-voltage switch and the second high-voltage switch. In said each circuit; the controller unit configured to provide pulses, which, when provided to an x-ray tube, result in the double pulsed x-ray source. In a first circuit from the plurality of circuits, the first terminal of the secondary winding is connected to the second terminal of the secondary winding of a subsequent circuit from the plurality of circuits; in every subsequent circuit from the plurality of circuits except for a last circuit from the plurality of circuits, the first terminal of the secondary winding is connected to the second terminal of the secondary winding of a subsequent circuit from the plurality of circuits and the second terminal of the secondary winding is connected to the first terminal of the secondary winding in a preceding circuit from the plurality of circuits; in the last circuit from the plurality of circuits, the second terminal of the secondary winding is connected to the first terminal of the secondary winding of a preceding circuit from the plurality of circuits.

In one instance, each circuit from the plurality of circuit includes a diode connected between the first terminal of the secondary winding of the transformer and the second capacitor, the second capacitor being connected between an output terminal of the diode and the second terminal of the secondary winding of the transformer; in the first circuit from the plurality of circuits, the second terminal of the secondary winding is connected to ground and an anode terminal of an x-ray tube is connected to the second terminal of the secondary winding in the transformer of the first circuit; in the last circuit from the plurality of circuits, the output terminal of the diode is also connected to a cathode terminal of the x-ray tube; the controller unit is also operatively connected to a filament control unit for the x-ray tube and to a current sensor sensing current to the anode terminal of the x-ray tube; the controller unit being configured to control pulse width, tube currents and voltages. (Although x-ray tubes, both grounded anode and bipolar, are available commercially, a description of x-ray tube can be found, for example, in U.S. Pat. No. 8,761,344, entitled SMALL X-RAY TUBE WITH ELECTRON BEAM CONTROL OPTICS, filed on Dec. 29, 2011, or U.S. Pat. No. 6,134,300, entitled MINIATURE X-RAY, filed on Nov. 5, 1998, or U.S. Pat. No. 6,128,367, filed on Jul. 22, 1998, all of which are incorporated by reference herein in their entirety and for all purposes.)

In one embodiment, the predetermined voltage is between 800 volts and 1500 volts. In another embodiment, the predetermined turn ratio is between 5:1 to 25:1. Embodiments in which the first high-voltage switch and the second high-voltage switch are triggered spark gaps (see, for example, Hofstra Group, high-voltage triggered spark gap specification) and embodiments in which the high-voltage switches are high voltage FET switches (for example, IXYS 4500V High Voltage Power MOSFETs) are both within the scope of these teachings. In one embodiment, the predetermined time for extinguishing pulses is between 0.5 microseconds and 1.5 microseconds.

In another instance, the double pulsed x-ray source 20 also includes a bipolar x-ray tube receiving a voltage between the second terminal of the secondary winding of the first circuit from the plurality of circuits and the first terminal of the secondary winding of the last circuit from the plurality of circuits 60.

An exemplary embodiment is presented herein below. It should be noted that these teachings are not limited by the exemplary embodiment. It was established that each of these pulses will have enough X-rays to provide high SNR. Based on the extensive search on existing sources, the Moxtek Ceramic X-ray tube is selected for the prototype because of its excellent properties. The Moxtek Ceramic X-ray tube selected for the project is rated as an average 50 W tube with a focal spot size of 80 μm and a cone angle of 30°. As per the design, the tube will produce two consecutive X-ray bursts, each 10 μs wide with in-between time adjustable from 10 to 100 μs (see FIG. 1-1*a*). The double pulse pattern can be repeated for up to 15 double pulses per second. The reduced duty cycle from the pulse pattern permits the tube operation at a significantly higher instantaneous power, exceeding 100 Watts. The design is aimed at operating the tube at 80 kVp with current of 1 mA during each X-ray burst.

Figure 4:
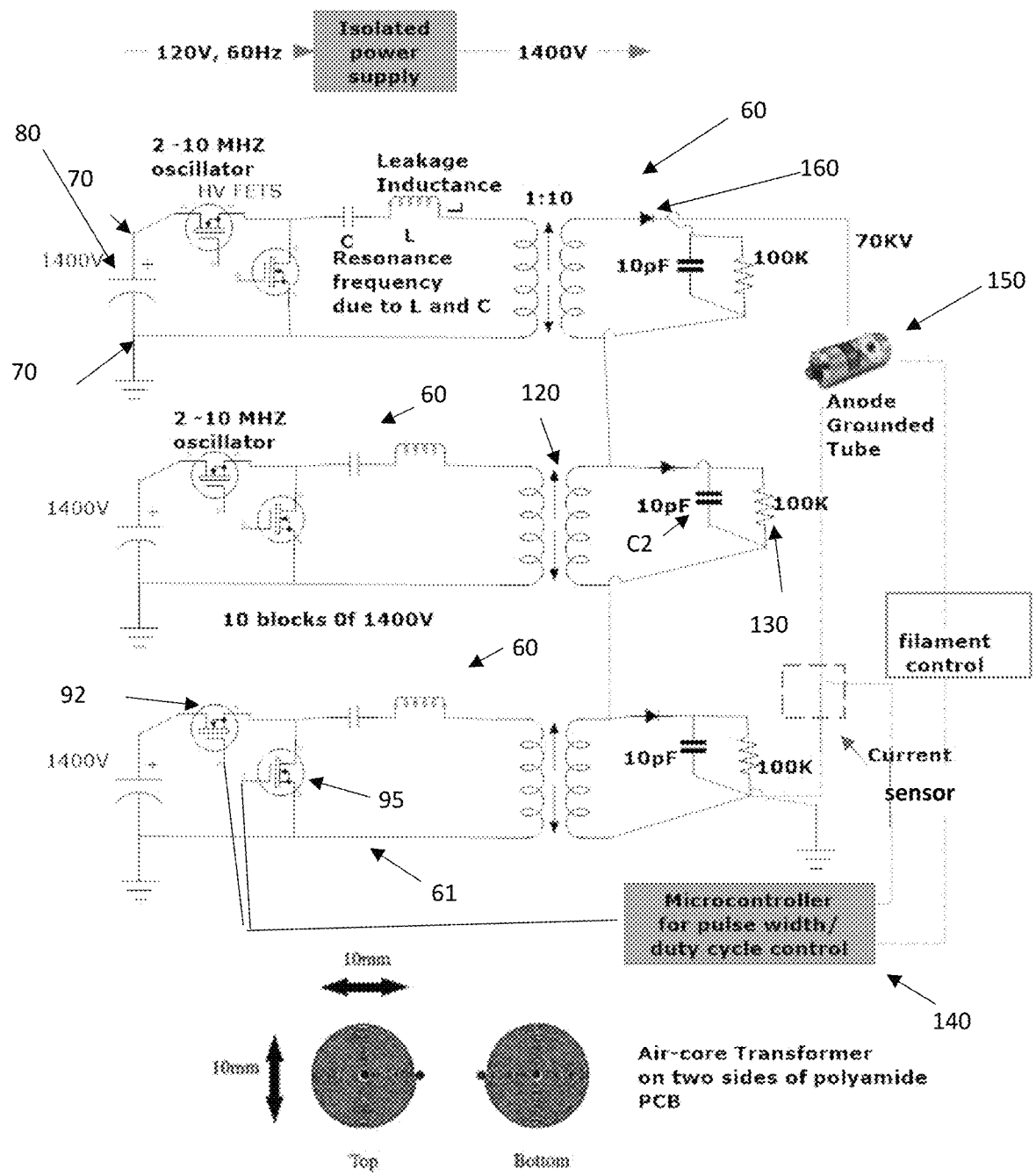
FIG. 4 shows a system block diagram of one embodiment of a double pulsed x-ray source of these teachings.

Herein below, a programmable pulse generator to generate X-ray pulses that are 10 μs in duration is described. These pulses can be 25 to 100 μs apart with a repetition rate of 15 double pulses per second. This is a novel concept that uses cascaded resonant air-core transformers to generate pulses vis-a-vis conventional methods, such as Cockcroft Walton voltage multipliers. The simplified system block diagram for this embodiment of the double-pulsed X-ray source of these teachings is shown in FIG. 4. A brief description of the embodiment shown in FIG. 4 is given below:
1. As isolated supply converts line voltage to 1400V or a greater voltage. This subsystem also generates lower voltages for the electronic control circuitry.
2. HV FETS consist of an array of high voltage, high speed switches to energize to create pulses of 2-10 MHz.
3. $L_{(n)}$ are leakage inductances of each of the 10 air-core transformers.
4. $C_{(n)}$ are resonant capacitors which in conjunction with the leakage inductances in (3) comprise of a resonant circuit to generate pulse widths of $\frac{1}{2}\pi\sqrt{LC}$ where L is the leakage inductance and C is the resonant capacitor. The width of the pulses can be adjusted with the resonant capacitors.
5. Diodes $D_{(n)}$ on the transformer's secondary are used for an anode grounded tube to generate a unipolar pulse. For a bipolar tube these diodes are unnecessary. The 100K resistor and 10 pF capacitor in parallel ensure that the output pulse extinguishes itself in about a microsecond.
6. The Tube is a MOXTEK 80 watt tube which is anode grounded.
7. The filament control is used to control the filament current, which in turn controls the tube current. Predictive control will allow the requisite amount of space charge to be generated for the tube, to prevent coronas.
8. The Controller unit controls the system, including data acquisition, pulse widths, tube currents and voltages. This controller will be connected to a laptop with a dashboard to control the system operation.

Referring to FIG. 4, in the embodiment shown therein three circuits 60 are shown. Each of the circuits 60 shown in FIG. 4 has a two terminal input port 70 and a DC voltage source 80 of a predetermined voltage (1400 V in the embodiment shown in FIG. 4). Each of the circuits 60 has the same structure. A first high-voltage switch 92, a high-voltage FET switch in the embodiment shown, is connected to the first terminal of the two terminal input port 70. A second high-voltage switch (a high-voltage FET switch in the embodiment shown) 95 is connected between an output of the first high-voltage switch 92 and the second terminal of the two terminal input port 70. A first capacitor C is connected between the output of the first high-voltage switch 92 and a first terminal of the primary winding of a transformer 120. A second terminal of the primary winding of the transformer 120 is connected to the second terminal of the two terminal input port 70. The first capacitor C and a leakage inductance of the transformer 120 constitute a resonant circuit. In the embodiment shown in FIG. 4, a diode 160 is connected to a first terminal of the secondary winding of the transformer 120. A second capacitor C2 is connected between an output of the diode 160, and the second terminal of the secondary winding of the transformer 120. Embodiments in which the second capacitor C2 is connected to a first terminal of the secondary winding of the transformer 120 (on a diode is not used). Are also within the scope of these teachings. A resistor 130 is connected in parallel with the second capacitor C2. The resistor 130, and the second capacitor C2 are selected such that output across the secondary windings of the transformer 120 is extinguished in a predetermined time, the predetermined time being about 1 µs in the embodiment shown. A controller unit 140 is operatively connected to the first high-voltage switch 92 and the second high-voltage switches 95. The first terminal of the secondary winding of the transformer 120 in the first circuit 61 is connected to the second terminal of the secondary winding of the second circuit and the first terminal of the secondary winding of the transformer 120 in the second circuit is connected to the second terminal of the secondary winding of the third circuit.

In the embodiment shown in FIG. 4, in the first circuit 61, the second terminal of the secondary winding is connected to ground and an anode of an x-ray tube 150 is also connected to ground. A first terminal of the secondary winding of the third circuit is connected to a cathode terminal of the x-ray tube 150. Embodiments in which diodes are not used and the second terminal of the secondary winding in the first circuit 61 is not connected to ground and a bipolar x-ray tube receiving a voltage between the second terminal of the secondary winding of the first circuit 61 and the first terminal of the secondary winding of the transformer 120 in the third circuit are also within the scope of these teachings.

Figures 5A, 5B, 5C, 5D:
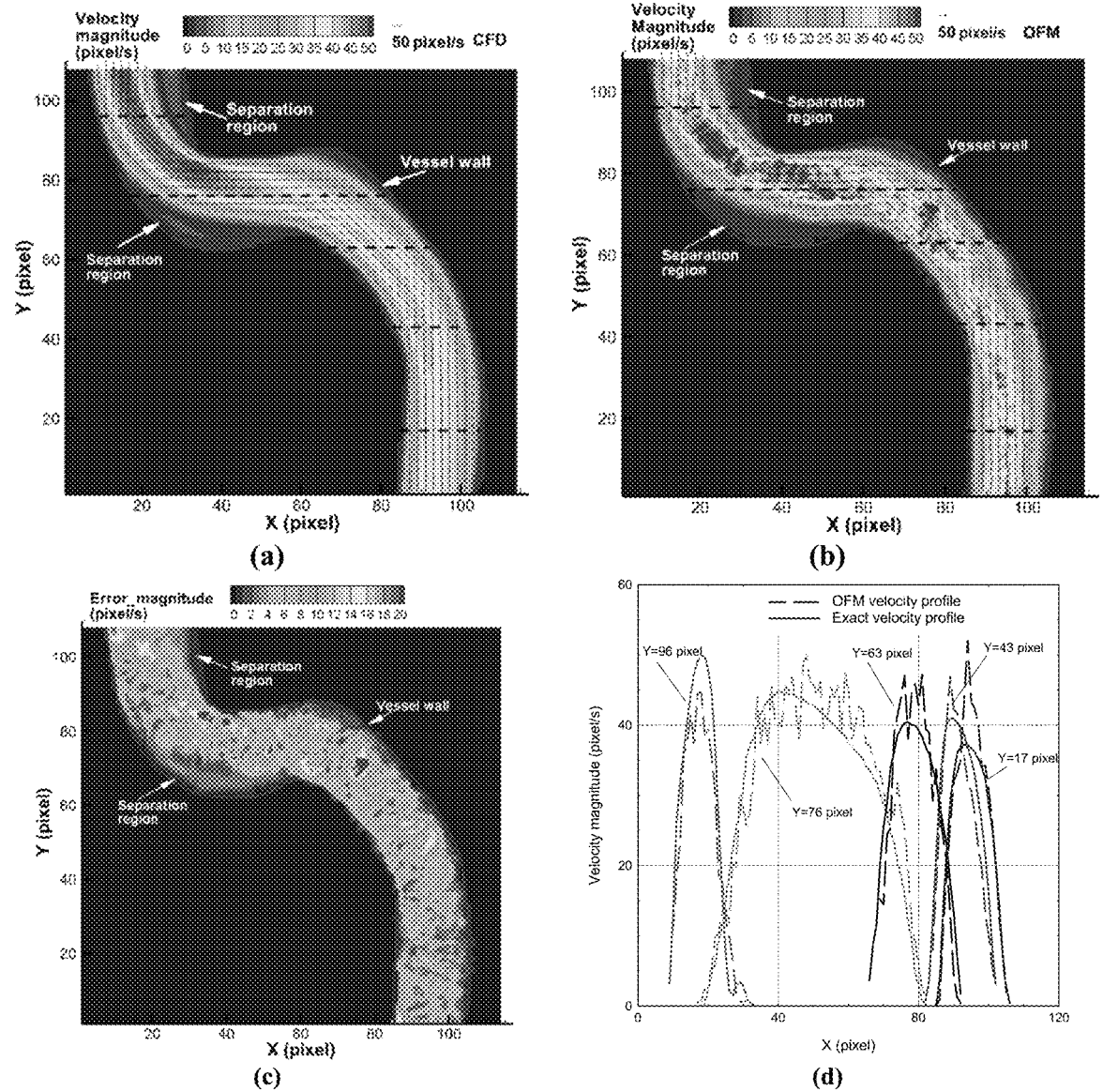
FIGS. 5a-5d show processed velocity maps obtained by the divergence compensatory OFM.

Implement Principles of Digital Subtraction Angiography
Development of Divergence Compensatory Optical Flow Method for Blood Flow Velocimetry Based on DSA A divergence compensatory Optical Flow Method was developed to calculate the velocity distribution from digital subtraction angiography (DSA) images of vascular flow. The non-zero divergence of velocity assumed due to the finite resolution of the image has improved the accuracy of the optical flow method (OFM). DSA images of intracranial arteries of humans were adopted to examine the accuracy of this novel method. Compared with traditional OFM, the current method always produced a better accuracy in processing the image pairs, in which the first image was a practical DSA image, and the second is created by simulating a given flow field. As presented in FIGS. 5A-5c, the processed velocity map by the divergence compensatory OFM shows an excellent agreement with the given velocity distribution. The error distribution map (FIG. 5c) and velocity profile comparisons at five locations also confirmed the good agreement. FIG. 5 (a) shows given velocity distribution for simulation; FIG. 5(b) shows processed velocity distribution using the divergence compensatory OFM; FIG. 5(c) shows error distribution; FIG. 5 (d) shows velocity profile comparison at five cross sections.) Some pre-process techniques, such as image intensification, Gaussian filtering and "image-shift", play important role in the improvement of accuracy as well.

Figure 6A:
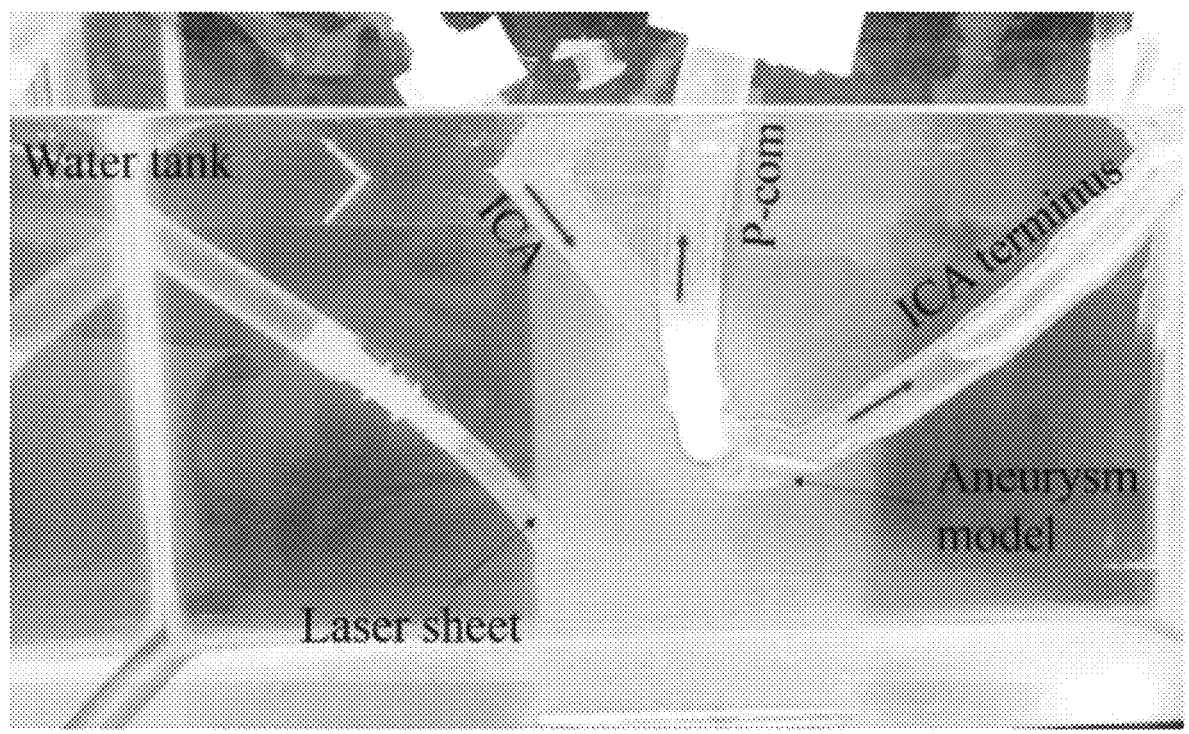
FIG. 6(a) shows silicone aneurysm model immersed in the water with laser sheet illumination.
Figure 6B:
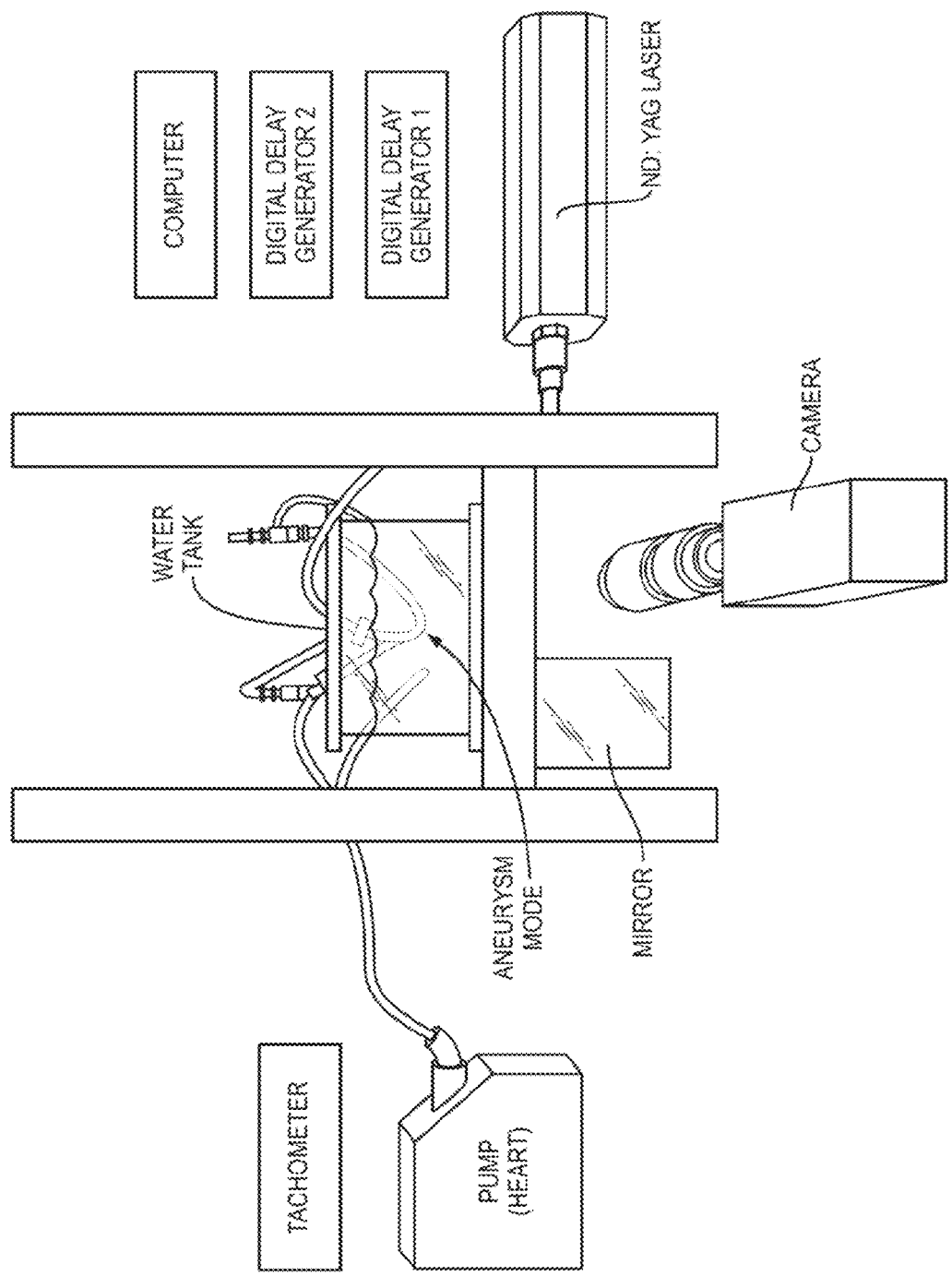
FIG. 6(b) shows experimental setup for PIV measurements on the aneurysm model.

PIV experiments on the physical aneurysm model.
Particle Image Velocimetry (PIV) serves as the gold-standard to validate the blood velocimetry technique based on DSA imaging. Patient-specific intracranial aneurysm models were created and manufactured by using 3D printing technique with silicone as the material, as shown in FIG. 6(a). It is completely transparent when it is immersed into the water. This allows the particle tracers (10 µm silver coated hollow glass balls) to be visible with the illumination of laser sheet (Nd: YAG). A CCD camera with a double-shutter function was used to capture two images when the laser sheet was shot through the field of interest. As shown in the setup picture (FIG. 6(b)), a laser tachometer was used to detect the moving phase of the pulsatile pump. (FIG. 6(a) shows silicone aneurysm model immersed in the water with laser sheet illumination (ICA: Internal Carotid Artery; P-com: Posterior Communicating Artery) FIG. 6(b) shows experimental setup for PIV measurements on the aneurysm model.)

Figure 7A:
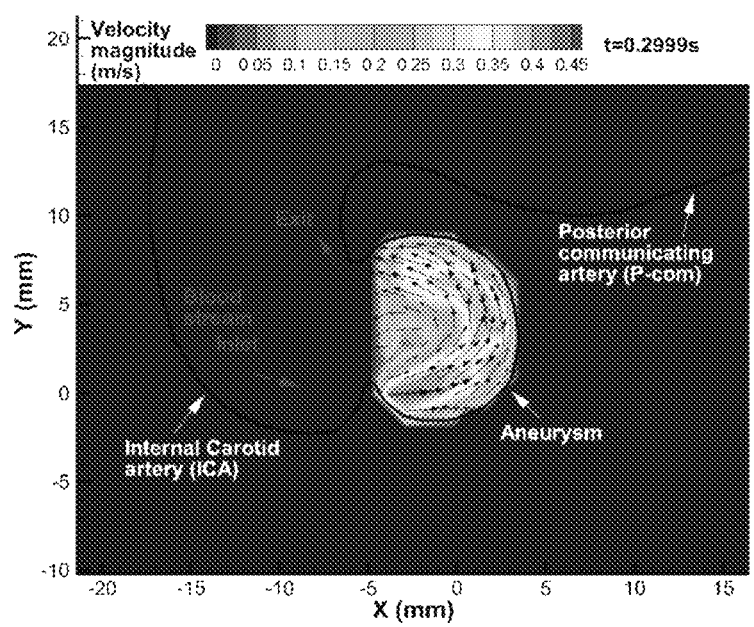
FIG. 7a-7d present the phase-locked averaged PIV measurements results.
Figure 7B:
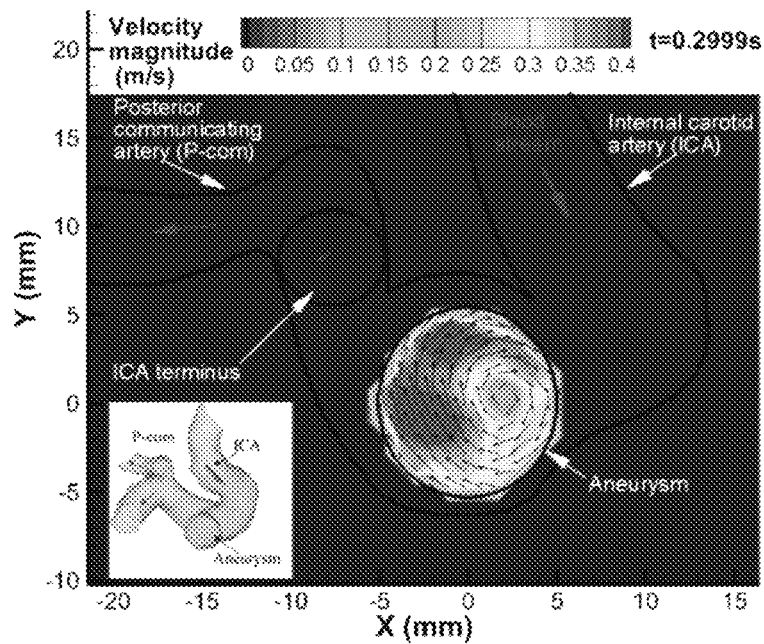
Figure 7C:
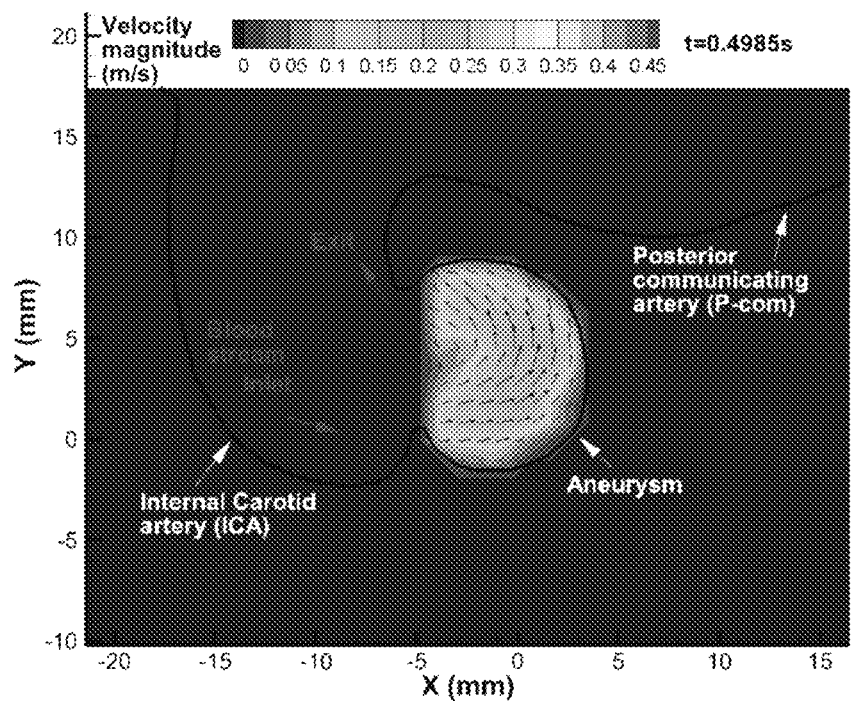
Figure 7D:
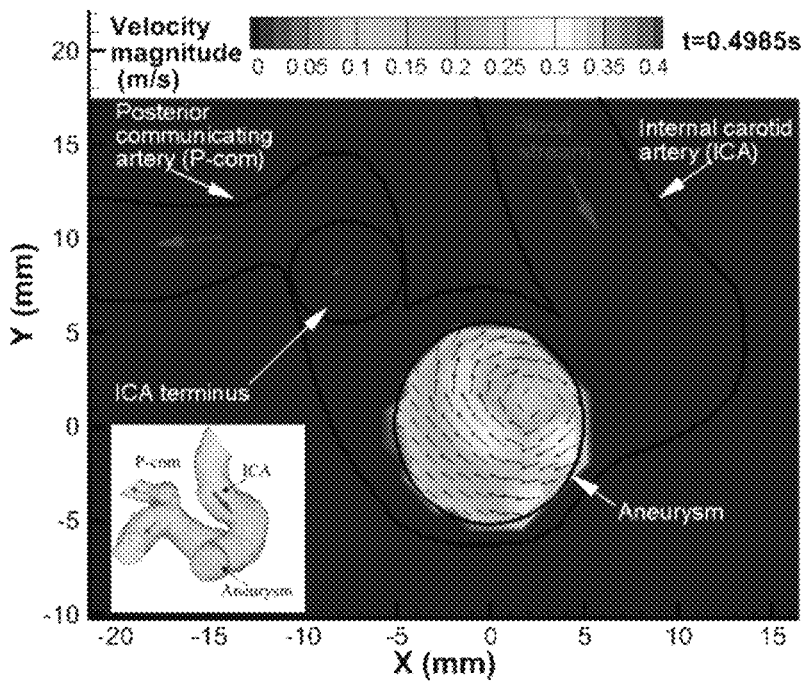

The TTL signal from the tachometer was used to synchronize the whole PIV system through two digital delay generators/synchronizers. A phase-locked averaged flow measurement can be obtained to filter out the random noise in the instantaneous velocity distributions. By adjusting the time delay, flow features at all phases during the pulsatile cycle can be acquired. For a pulse rate of 60 cycles/minute, FIG. 7d presents the phase-locked averaged PIV measurements results at time instants of 0.2999 s and 0.4985 s in a cycle for two different cross sections (vertical cross and spanwise cross). These results will be used for validating the flow measurements by using the X-ray velocimetry technique applied on the same aneurysm model Develop and Validate Improved OFM for In Vitro and In Vivo Blood Velocity and WSS Mapping A computer code based was developed on improved OFM is used to recover the velocity map from images in three levels, i.e. synthetic images of motion (mostly completed in the pilot study), in vitro fluid flow images in physical models and in vivo blood flow in vasculatures. The improved OFM and PIV technique is applied to the DSA images and particle images respectively, to quantify the flow field in the same ROI of the vascular model. Visipaque 300 contrast agent is injected through a 5 F Terumo angle taper catheter for X-ray imaging. Silver-coated hollow glass spheres (Dantec Dynamics, Inc.) is used as tracers for the PIV test. The flow velocity distribution within vascular models produced from both methods is analyzed and compared to validate the accuracy of the improved OFM. Digital flow meters to measure the flow rate is used as the second validation source. Animal blood and vessels purchased from a local slaughterhouse near WSU is used for these experiments. The high frame rate X-ray imaging system is used to conduct imaging of the flow in physical models and in vivo blood vessels. The fluid used in the study is animal blood and a mixture of glycerin (59.1%) and water (40.9%), as used in most studies, to approach the blood density of 1060 kg/m3 and kinematic viscosity of $(3-4) \times 10-6$ m2/s. PIV can only be applied to the transparent models with clear fluid mixture while X-ray system can be applied to both in vitro and in vivo models with either fluid. The image quality for X-ray imaging in terms of brightness pattern is determined mainly by the contrast agent distribution. It indicates that the control of the contrast injection process will play a key role in the control of the image quality. Different injection method is designed and tested to gain the optimum contrast injection. The effect of the injection rate, distance from the ROI on the flow characteristics is determined through the in vitro experimental study. In the conduction of the experiment, the fluid temperature, density, viscosity, Reynolds number and Womersley number is well controlled to get close to in vivo conditions of endovascular flow.

Figure 8:
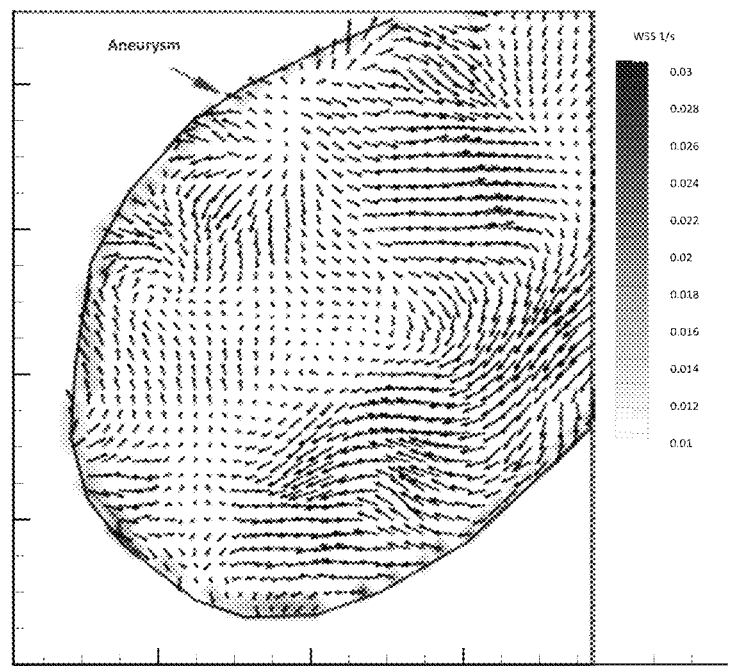
FIG. 8 shows detailed velocity distribution in the ROI and WSS distribution.

The improved OFM is validated at three levels, i.e. synthetic image validation, in vitro experimental validation, in vivo experimental validation, with the uncertainty level less than 10%. The detailed velocity distribution in the ROI and WSS distribution is obtained by using the improved OFM, as shown in FIG. 8 from a preliminary study on intracranial aneurysm. This study also identifies significant factors that determine the successful recovery of blood velocity from in vitro to in vivo experiments. The error analysis is correlated with regard to the studied parameters of image quality, e.g., the characteristic gradient of intensity, time interval for image acquisition, etc.

The pulsatile pattern of the contrast agent in the blood flow favor OFM. The error analysis is also correlated with physical parameters during catheterization, such as the contrast flow rate, the formality of contrast injection (continuous injection, pulsed injection, oblique injection). Once the improved OFM is validated, all flow measurements can be made by X-ray angiography in-80 instead of PIV. In vitro experiments are not restricted by transparent models, which has been the limit of all current model studies because experimental techniques such as PIV, LDV require clear optical 60 access of the flow.

The following are incorporated by reference herein in their entirety and for all purposes:

Fouras, A., Kitchen, M. J., Dubsky, S., Lewis, R. A., Hooper, S. B. and Hourigan, K. 2009. The past, present, and future of x-ray technology for in vivo imaging of function and form. *Journal of Applied physics*, 105:102009.

Rohde, K. S., Lammbrou, T., Hawkes, D. J. 2005. Novel approaches to the measurement of arterial blood flow from dynamic digital x-ray images. *IEEE Trans Med Imaging*, 24:500-13.

Park, H., Yeom, E., Seo, S. J., Lim, J. H., Lee, S. J. 2015. Measurement of real pulsatile blood flow using X-ray PIV technique with $CO_2$ microbubbles. *Scientific Reports*, 5:8840.

Hanwook Park, Eunseop Yeom & Sang Joon Lee, 2016, X-ray PIV measurement of blood flow in deep vessels of a rat: An in vivo feasibility study, *Scientific Reports*, 6:19194

Seifalian, A., Hawkes, D., Hardingham, C., Colchester, A., and Reidy, J. 1991. Validation of a quantitative radiographic technique to estimate pulsatile blood flow waveforms using digital subtraction angiographic data. *J Biomed Eng*, 13:225-33.

Bartram R. H., et al, "Afterglow suppression and non-radiative charge-transfer in CsI:Tl,Sm," *IEEE Trans. Nucl. Sci.*, 55(3), Part 2, pp 1232-1236, (2008).

Nagarkar V. V., et al, "Scintillation properties of CsI:Tl crystals codoped with $Sm^{2+}$," *IEEE Trans. Nucl. Sci.*, 55(3), pp 1270-1274 (2008).

Nagarkar V. V., et al, "Suppression of afterglow in microcolumnar CsI:Tl by codoping with $Sm^{2+}$: Recent advances," *IEEE Trans. Nucl. Sci.*, 56(3), pp 565-569 (2009).

Ovechkina E. E., S. R. Miller, V. Gaysinskiy, C. Brecher, V. V. Nagarkar, Effect of $Tl^+$ and $Sm^{2+}$ Concentrations on Afterglow Suppression in CsI:Tl,Sm Crystals, *IEEE Trans. Nucl. Sci.*, vol. 59, no. 5, pp 2095-2097, 2012.

Nagarkar V V, Gaysinskiy V, Ovechkina E E, Miller S R, Brecher C, Lempicki A, and Bartram R H, "Scintillation properties and applications of reduced-afterglow co-doped CsI:Tl", *Proc. SPIE* 6707, 67070D (2007).

Nagarkar V V, Gaysinskiy V, Ovechkina E E, Miller S R, Cool S, Thacker S, Brecher C, and Lempicki A, "Suppression of afterglow and hysteresis in CsI:Tl by codoping with $Sm^{2+}$: Fabrication of microcolumnar films for high-resolution high-speed imaging," Presented at *IEEE NSS/MIC* 2007, Hawaii, October 2007.

Thacker S. C., et al, "Low-afterglow CsI:Tl microcolumnar films for small animal high-speed microCT," *Nucl. Instrum. Meth. in Phys. Res. A* 604 (2009) 89-92.

Thacker S. C., et al, "Characterization of the new co-doped CsI microcolumnar films for high-speed radiographic imaging," *Proc. SPIE* 6913, 69130Q (2008).

V. Nagarkar et. Al., "Scintillator Materials with Reduced Afterglow and Method of Preparation," U.S. Pat. No. 7,180,068, Feb. 22, 2007.

C. Brecher, V. Nagarkar, "Scintillation materials with reduced afterglow and method of preparation," U.S. Pat. No. 7,759,645, Issue Date Jul. 20, 2010

Bipin Singh, Stuart R. Miller, Harish B. Bhandari, Rita Graceffa, Thomas C. Irving, Vivek V. Nagarkar, "High-speed detector for time-resolved diffraction studies," Journal of Physics: Conference Series 425 (2013) 092005; doi:10.1088/1742-6596/425/9/092005.

Characterizing Ballistic Impacts

The 3D Fragment Mapping System

Figure 9:
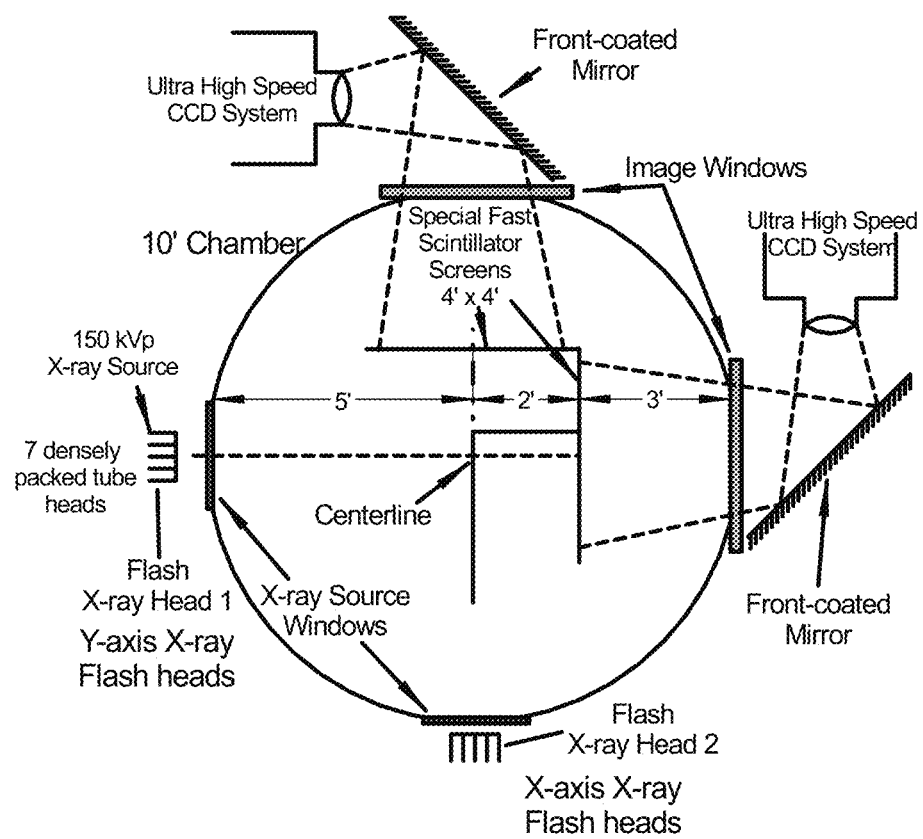
FIG. 9 shows a schematic of the ultra-fast imaging system for explosive fragment mapping.

The 3D fragment mapping system uses two identical X-ray imaging systems oriented orthogonally to each other as shown in FIG. 6. The orthogonality of system orientation is not critical, but preferred for ease of calibration and the 3D data reconstruction. FIG. 9 shows a schematic of the ultra-fast imaging system for explosive fragment mapping. The system provides center of mass, eccentricity, 2D bounds, and the velocity of the fragments. The orthogonality of system orientation is not critical, but preferred for ease of calibration and the 3D data reconstruction. Each imaging channel consists of a triggered flash X-ray source capable of producing 20 to 50 ns bursts of 150 kVp X-rays, a HSS-1 scintillator screen, and an image-intensified multi-frame high-speed CCD/CMOS camera. The HSS-1 converter screen used in conjunction with the flash X-ray generators is at least 122×122 cm$^2$ (48"×48") in area, provides over 85% absorption of the incident 150 kVp X-rays, and has a spatial resolution of at least 5 lp/mm or 100 µm. To ensure blur-free high resolution imaging, the scintillator decay time is <1 µs and it has no persistence in the µs time regime. The screens are mounted on a plywood panel, and the light generated by the interactions of X-rays into the scintillator screen is imaged by the intensified high-speed Photron SA4 camera positioned at secured location. This camera provides 1024× 1024-pixel resolution and inter-exposure times from 5 ns to 20 ms. All system components are portable, rugged, and modular. As shown in FIG. 6, a front coated mirror oriented at 45° with respect to the scintillator will transfer X-ray images to the camera.

Initially a calibration fixture similar to the one at Arnold Engineering Development Complex (AFDC) and made of Lexan with lead balls as targets, will be imaged and these data will be used to calibrate the system for 3D reconstruction of the parameters from pairs of images. This calibration process is fully automated, and will have to be performed only once before system use. During the actual experiments, the explosion event will be used to trigger the X-ray sources and the CCD cameras. The flash X-ray sources and the CCD camera image capture will be synchronized to ensure that the X-rays are fired during the CCD image integration interval. The software instantaneously analyzes the images to yield the precise information about the fragment shape, size, and 3D velocity distribution in near real-time.

The fragment tracking is done using the ProAnalyst FPE software from Xcitex, which is performed on a fee-for-service basis.

Time Resolution and Measurement Accuracy

Fragments moving at a velocity of 1,000 m/s will require approximately 1.22 ms to travel the 122 cm (48 inch) length of the scintillator screen. Using the microfocus continuous X-ray source, images can be acquired continuously using the Photron SA4 camera at framing rates up to 500,000 fps. For example, if the camera is operated at 5,000 fps, one image will be acquired every 200 µs. Thus, the camera speed does not pose any difficulty in capturing the entire explosion event at the desired speed.

Since the CCD pixel resolution is 1024×1024 pixels, and the scintillator length is 122 cm, the system resolution at the scintillator screen will be 122 cm/1024 or 1.19 mm. Thus, with single pixel accuracy, the system should be able to measure the particle trajectory with an accuracy of 1.19 mm. Note that the resolution can be scaled by reducing the active imaging area.

Similar to the above calculation, assuming a single pixel accuracy of the imaging system, the accuracy in reading angles will be $\tan^{-1}(0.119/122)=0.055°$. Again this will somewhat degrade during actual firing and based on the other experimental conditions, our worst-case estimate of accuracy in reading angles is 0.055°.

It should be noted that imaging a 122 cm screen with 0.119 cm accuracy corresponds to a measurement accuracy of 0.09%, which is a very high accuracy and precision measurement.

Description of the System Components

Bright, High Resolution, Fast Scintillator Screens

At high frame rates almost any imaging application is inherently light-starved. The problem is exacerbated when the source of light is the passive output of an X-ray scintillator screen. Thus, in such applications a premium is placed on the X-ray-to-light conversion efficiency, the speed of emission or decay time, persistence, and the X-ray stopping power of the scintillator, making it the key component of the high speed X-ray imaging system. Furthermore, the screen must be manufactured in the required large areas of 122×122 cm$^2$ while maintaining low cost and high spatial resolution.

In previous work, scintillator screens made of several different materials that would satisfy all the requirements of a high speed imaging application have been evaluated. Table 4 lists these candidate materials and their scintillation properties. Although screens made from any of these materials would work for this application, from the point of view of performance and the cost per unit area, the Gd$_2$O$_2$S(Pr) and HSS screens are the most suitable choice. For example, the microcolumnar CsI(Tl) screens manufactured by RMD would be the brightest and would provide the best spatial resolution in the range of 5 to 7 lp/mm (100 µm to 70 µm range), but a CsI screen of required size would cost well over $15,000 compared to $1,000 or so for the Gd$_2$O$_2$S(Pr) and HSS screens.

TABLE 4

Important properties of scintillators for high-speed imaging.

| Scintillator Material | Decay Time (ns) | After-glow | Conversion Efficiency (photons/MeV) | Peak Emission (nm) | Screen Density (g/cc) |
|---|---|---|---|---|---|
| Microcolumnar CsI(Tl) | 680 | Tens of µs | 61,000 | 540 | 4.3 |
| Gd$_2$O$_2$S(Pr) | 2700 | No | 49,000 | 540 | 3.9 |
| RMD's HSS-1 | 480 | No | 45,000 | 390 | 5.2 |
| Lu$_2$SiO$_5$(Ce) or LSO | 40 | No | 30,000 | 420 | 3.9 |
| Y$_3$Al$_5$O$_{12}$(Ce) or YAG | 88 | No | 19,700 | 550 | 2.7 |
| CdWO$_4$ | 2500 | No | 28,000 | 470 | 3.4 |

Both Gd$_2$O$_2$S(Pr) and HSS screens are fabricated using the slurry technique. Screens measuring 70 to 120 mg/cm$^2$ in thickness are fabricated and evaluated in terms of their decay time, afterglow, light yield, and spatial resolution. Screens of such high thickness are necessary to provide over 80% absorption efficiency for the 150 kV X-rays. A key to our success is to maintain the required high level of light output and high spatial resolution in spite of such a high thickness. However, since the fragments to be tracked are expected to be between 100 µm and several centimeters in size, our imaging system has adequate spatial resolution for most of the fragments. As such, the scintillator's spatial resolution may be relaxed. On the other hand, since the fragments velocities may be ~1,000 m/s, it is particularly important to obtain images with a high SNR. This means that the generated images must be as bright as possible. Therefore, after the initial scintillator screen thickness of ~100 mg/cm$^2$, thicker scintillator screens to provide higher X-ray absorption efficiency are also fabricated, thereby providing brighter images with higher SNR. Such thicker screens still have the spatial resolution required for the imaging application. However, since there is self-absorption in thicker scintillator screens, a judicious trade-off is made between the absorption efficiency, light yield, and spatial resolution.

Flash X-Ray Sources

The double-pulsed X-ray source described herein above, and shown in FIG. 1, is used.

High Resolution High Speed CCD Camera

The existing Photron SA4 high speed intensified CCD can be used. The SA4 system uses a 1K×1K CMOS coupled to a GEN III image intensifier. The camera design allows the front-end sensitivity to be maximized as there is no beam splitter used and thus each frame sees all the available light from the event. This in turn permits the system to run at lower gain, which maintains better image quality and better dynamic range. The images are transferred to adjacent image storage areas after each frame.

The camera has an option to use either an S20 or S25 photocathode with the intensifier. The S20 photocathode with a peak sensitivity of 390 nm, which is well matched to the peak light emission of the HSS-1 scintillator to be used for imaging, is used. The intensifier gain may be varied from 1 to 10,000 depending on the emission intensity of the screen and the required contrast in the image. Furthermore, the camera speed is such that two (or more) consecutive high-resolution images can be obtained with the required timing resolution.

This camera can accept and generate a high precision timing signal for synchronization with the external devices. For our application, the camera can be triggered after the predetermined time delay after the projectile is fired. Also, the time delay between the two consecutive image frames can be precisely adjusted.

During recent years, tremendous technological progress has been made in the detector technologies, resulting in extremely high-performance detectors now becoming commercially available. Therefore, newer high-speed cameras available from various manufacturers will be considered. Some of the possible candidate camera systems are listed in Table 5.

TABLE 5

Potential commercial microsecond timing resolution cameras

| Manufacturer | Camera Model | Speed (fps) | Pixels | Number of Frames |
|---|---|---|---|---|
| Specialized Imaging | Cerberus | 7.2M | 1360 × 1024 | 8 |
|  | SimX | 1B | 1360 × 1024 | 8 |
|  | SimD | 1B | 1360 × 1024 | 8 |
| Invisible Vision | UHSi 12 | 200M | 1000 × 860 | 12 |
| Photron | Fastcam SA-Z | 2.1M | 1024 × 1024 | 200K |
|  | Fastcam SA-X2 | 1M | 128 × 8 | 62K |
| Vision Research | V1610 | 1M | 128 × 16 |  |
|  | V711 | 1.4M | 128 × 8 |  |
|  | V611 | 1M | 128 × 8 |  |
| Shimadzu | HPV-X | 10M | 400 × 250 | 256 |
|  | HPV-2 | 1M | 312 × 260 | 100 |

3D Fragment Measurement and Analysis Software

The fragment parameters will be measured in a calibrated space using a comprehensive tool such as the ProAnalyst 3D FPE available from Xcitex, Inc. Initially a calibration fixture similar to the one at AEDC and made of Lexan with lead balls as targets, will be imaged and these data will be used to calibrate the system for 3D reconstruction of the parameters from pairs of images. This calibration process will be fully automated, and will have to be performed only once before system use. During the actual experiments, a signal generated by the projectile intercepting a light beam will provide the trigger for both the flash X-ray sources and the CCD cameras. The multi-anode flash X-ray sources from each channel will be precisely timed and synchronized with the projectile motion and with the CCD, and will be used to illuminate the impact scene. Two such systems oriented orthogonally to each other will be used. Using the two projections, the ProAnalyst software will be used for mapping the fragment, computing fragment velocity profile, and displaying data in 3D plots. Although ProAnalyst 3D is ideally suited for test ranges, ballistics tests, dynamic ram tests, etc., several modifications are needed before it can be incorporated in the imaging system. During the beginning of the project, we will work closely with Xcitex engineers to determine and implement the necessary changes in this package. Specifically, in the current commercial version of the software, only 250 particles can be tracked in a plane. This capability is extended to 1000 particles to meet the needs of the application. When completed, this software will compute accurate 3D position and orientation using pairs of flash X-ray images. Tools for lens distortion correction will be included in the analysis algorithms for improved accuracy. The results will be instantaneously displayed in an interactive 2D and 3D graphing format. The pair of optical images of the projectile with separated sabot used for computation is shown on the left. The graphs on the right show the 3D coordinate computation and display. The bottom portion of the display shows numerical values of various projectile parameters These data are presented in both real world coordinates and relative frame coordinates, and will also be stored in standard formats for further analysis.

An important feature of this software is its flexible calibration options, which allow users to use their own fixture or one of the pre-designed fixtures. Also, the software determines optimal calibration automatically. We use a calibration fixture similar to the on at AEDC, which will be made of Lexan with lead balls as targets. Once the software modifications necessary for the dynamic fragment mapping application are determined, and included.

Fabrication and Evaluation of Large Area Scintillator Screens

Scintillator Fabrication

As previously noted, $Gd_2O_2S(Pr)$ and HSS-1 screens are expected to provide the best balance between scintillator performance and price per unit area and are expected to provide the required performance in terms of spatial resolution, light output, and X-ray absorption efficiency. These screens in the compositions required to achieve the fast timing properties are not commercially available. As such, both the $Gd_2O_2S(Pr)$ and HSS screens are fabricated. Initially, 70 to 120 mg/cm² thick scintillator films that will provide high light yield and ~80% absorption of 150 kV X-rays are developed, while maintaining the spatial resolution of 5 to 7 lp/mm. However, since the fragments to be tracked are expected to be ~1 cm³ in size, our imaging system will have more than adequate spatial resolution. As such, the scintillator's spatial resolution may be relaxed. On the other hand, since the fragments velocities may be ~1,000 m/s, it is particularly important to obtain images with a high SNR. This means that the generated images must be as bright as possible. Therefore, after the initial scintillator screen thickness of ~100 mg/cm², we will also fabricate thicker scintillator screens to provide higher X-ray absorption efficiency, thereby providing brighter images with higher SNR. However, since there is self-absorption in thicker scintillator screens, a judicious trade-off will be made between the absorption efficiency, light yield, and spatial resolution.

Both the $Gd_2O_2S(Pr)$ and HSS-1 screens will be fabricated using the slurry technique where the material in its powder form is mixed with an appropriate amount of urethane binder and the resulting slurry is uniformly coated onto a suitable substrate. To enhance the light yield, polymer substrates pre-coated with a reflective layer will be used. The powdered materials required for this process will be purchased from Nichia Chemical Corp., N.J. Specifically, approximately 5 kg of the scintillator powder with ~10 to 15 μm particle size and appropriate dopant concentration will be purchased. The screens will be coated and dried in a clean room environment and will subsequently be laminated to provide a protective coating. The screen composition is varied by varying the binder concentration in the slurry in an effort to maximize the light yield and the spatial resolution. Using the optimized composition, up to 60×60 cm² scintillators are fabricated on commercially available substrates.

Evaluation of the Initial Scintillator Screens
Film Morphology

The morphology of the scintillator screens is studied using scanning electron micrographs (SEM) of the interior structures. The film packing density and the distribution of the particle size within the films are critical parameters that determine the screen performance. The micrographs provide the necessary information which will be correlated with the screen performance, and the resulting data will be used as a feedback to further improve fabrication processes.

Scintillator Characterization Using X-Rays

The light output, SNR, spatial resolution, and overall noise performance of the scintillator screens will be evaluated at RMD by coupling them to a CCD detector dedicated for such purposes. The current imaging detector consist of a 1K×1K CCD with a fast f/0.9 lens which allows easy coupling of the scintillator screens to the sensor. With its 16 μm pixel size, the CCD camera has a Nyquist limiting frequency of over 30 lp/mm, a performance that is more than adequate for the testing. These studies are performed using the tungsten target (30 to 140 kVp) X-ray generator equipped with a suitable shutter mechanism.

Light output measurements is conducted by coupling various scintillators to the CCD and exposing them to a flood field of incident X-rays. The average value of the light intensity in analog-to-digital units (ADUs) and the standard deviation over a region of interest is quantified and used to calculate the intensity and SNR.

The spatial resolution of the scintillators is evaluated by imaging a standard tapered line pair phantom that allows measurements of contrast transfer function (CTF(f)) in the range of 1 to 10 lp/mm. These data give a quantitative measure of scintillator spatial resolution as a function of spatial frequency, which is useful in predicting the ultimate detector resolution.

Optical Characterization of the Scintillator Decay Properties
Spectral Characterization The X-ray excited emission spectra of various scintillator samples will be measured using equipment and instrumentation at RMD. The 40 to 150 kVp tungsten target X-ray source will be used to excite the sample under investigation. To generate the required flux at the sample, the X-ray generator will be operated at 140 kV with 20 mA current. The resulting scintillation light is collected in a MacPherson model 234/302-0.2 m monochromator that separates the light into its wavelength components. The intensity of the selected wavelength is registered using an RCA model C31034 photomultiplier tube (PMT). The operation of the whole instrument including the X-ray trigger, the rotation of the monochromator to select the wavelengths, and the data acquisition and analysis is software controlled. The spectral emission data along with the known CCD spectral response curve is used to estimate the signal strength and the expected SNR in the detector. These data is useful in selecting the best scintillator screen for the application.

The following are incorporated by reference herein in their entirety and for all purposes:

Nagarkar, V. V., S. V. Tipnis, V. Gaysinskiy, S. R. Miller, and I. Shestakova, "High-speed digital radiography using structured CsI screens," *Nucl. Inst. Meth. Phys. Res. B* 213, 476-480, 2004.

Nagarkar, V. V., Tipnis, S. V, Gupta, T. K., Miller, S. R., Gaysinskiy, V., Klugerman, M., Squillante, M. R., Entine, G., and Moses, W.W., "High Speed X-ray Imaging Camera Using Structured CsI(Tl) Scintillator," *IEEE Trans. Nucl. Sci.* 46(3), 1999.

V. V. Nagarkar, B. Singh, S. Miller, L. Campbell, R. Bishel, and R. Rushing, "A modular high precision digital system for hypervelocity projectile performance measurements," *Proc. SPIE* 6978, 697808 2008.

S. Miller, B. Singh, G. Entine, V. V. Nagarkar, L. Campbell, R. Bishel, and R. Rushing, "Ultra-High-Speed X-Ray Imaging of Hypervelocity Projectiles," *Nucl. Instr. Meth. A* 648(1), pp. S293-S296, 2011.

V. V. Nagarkar, T. K. Gupta, S. R. Miller, Y. Klugerman, M. R. Squillante, and G. Entine, Structured CsI(Tl) Scintillators for X-ray Imaging Applications. *IEEE Trans. Nucl. Sci*. Vol. 45, No. 3, June (1998).

V. V. Nagarkar, V. Gaysinskiy, I. Shestakova, S. Taylor, G. Entine, Thick Microcolumnar CsI(Tl) Films for Small Animal SPECT, presented at the IEEE 2004, Rome, Italy October 16-22, 2004.

V. V. Nagarkar, S. V. Tipnis, V. Gaysinskiy, S. Miller, Y. Klugerman, and P. O'Dougherty, High Speed X-Ray Imaging Camera for Time Resolved Diffraction Studies, *IEEE Trans. Nucl. Sci*. (2002).

V. V. Nagarkar, S. R. Miller, S. V. Tipnis, A. Lempicki, C. Brecher, H. Lingertat, "A New Large Area Scintillator Screen for X-Ray Imaging", NIM B, 213, pp. 250-254, (2004)

S. R. Miller, S. V. Tipnis, I. Shestakova, V. V. Nagarkar, "High-performance scintillator screen for medical imaging applications," SPIE Vol. 5541 p. 133-140, August (2004).

Although the invention has been described with respect to various embodiments, it should be realized these teachings are also capable of a wide variety of further and other embodiments within the spirit and scope of these teachings.

The invention claimed is:

1. A double pulsed X-ray source comprising:
an X-ray tube;
a high-voltage source comprising a plurality of circuits, each circuit from the plurality of circuits comprising:
a two terminal input port;
a DC voltage source of a predetermined voltage connected between a first terminal of the two terminal input port and a second terminal of the two terminal input port; the first terminal of the two terminal input port being connected to a positive voltage terminal of the DC voltage source and the second terminal of the two terminal input port being connected to a ground terminal of the DC voltage source;
a first high-voltage switch connected to the first terminal of the two terminal input port; a second high-voltage switch connected between an output terminal of the first high-voltage switch and the second terminal of the two terminal input port;
a first capacitor;
a transformer having a primary winding and a secondary winding, and having a predetermined turn ratio;
the first capacitor being connected between an output terminal of the first high-voltage switch and a first terminal of the primary winding of the transformer; a second terminal of the primary winding of the transformer being connected to the second terminal of the two terminal input port; the first capacitor and a leakage inductance of the transformer constitute a resonant circuit;
a second capacitor connected from a first terminal of the secondary winding of the transformer to a second terminal of the secondary winding of the transformer; and
a resistor connected in parallel with the second capacitor; the second capacitor and the resistor configured to extinguish an output in a predetermined time;
and a controller unit operatively connected to the first high-voltage switch and the second high-voltage switch; the controller unit being configured to provide pulses, which, when provided to the X-ray tube, result in the double pulsed X-ray source;
in a first circuit from the plurality of circuits, the first terminal of the secondary winding is connected to the second terminal of the secondary winding of a subsequent circuit from the plurality of circuits;
in every subsequent circuit from the plurality of circuits, except for a last circuit from the plurality of circuits, the first terminal of the secondary winding is connected to the second terminal of the secondary winding of a subsequent circuit from the plurality of circuits and the second terminal of the secondary winding is connected to the first terminal of the secondary winding in a preceding circuit from the plurality of circuits;
in the last circuit from the plurality of circuits, the second terminal of the secondary winding is connected to the first terminal of the secondary winding of a preceding circuit from the plurality of circuits.

2. The double pulsed x-ray source of claim 1, wherein said each circuit from the plurality of circuits comprises a diode connected between the first terminal of the secondary winding of the transformer and the second capacitor, the second capacitor being connected between an output terminal of the diode and the second terminal of the secondary winding of the transformer;
wherein, in the first circuit from the plurality of circuits, the second terminal of the secondary winding is connected to ground and an anode terminal of an x-ray tube is connected to the second terminal of the secondary winding in the transformer of the first circuit;
wherein, in the last circuit from the plurality of circuits, the output terminal of the diode is also connected to a cathode terminal of the x-ray tube; and wherein
the controller unit is also operatively connected to a filament control unit for the x-ray tube and to a current sensor sensing a current to the anode terminal of the x-ray tube; the controller unit being configured to control pulse width, x-ray tube currents and voltages.

3. The double pulsed x-ray source of claim 1, wherein the predetermined voltage is between 800 volts and 1500 volts.

4. The double pulsed x-ray source of claim 1, wherein the predetermined turn ratio is between 5:1 to 25:1.

5. The double pulsed x-ray source of claim 1, wherein the first high-voltage switch and the second high-voltage switch are triggered spark gaps.

6. The double pulsed x-ray source of claim 1, wherein the first high-voltage switch and the second high-voltage switch are high voltage FET switches.

7. The double pulsed x-ray source of claim 1, wherein said predetermined time is between 0.5 microseconds and 1.5 microseconds.

8. The double pulsed x-ray source of claim 1, further comprising a bipolar x-ray tube receiving a voltage between the second terminal of the secondary winding of the first circuit from the plurality of circuits and the first terminal of the secondary winding of the last circuit from the plurality of circuits.

9. An imaging system comprising:
a double pulsed x-ray source of claim 1 configured to illuminate a flowing fluid;
a scintillator configured to receive x-rays from the double pulsed x-ray source after illuminating the flowing fluid;
a detector; and
an optical unit configured to deliver an output from the scintillator to the detector.

10. The imaging system of claim 9, wherein the scintillator comprises a micro-columnar, low afterglow scintillator; and wherein the optical unit comprises:
a fiber-optic faceplate receiving the output from the micro-columnar, low afterglow scintillator; and
a fiberoptic taper optically operatively connected to the fiber-optic faceplate and configured to deliver the output from the micro-columnar, low afterglow scintillator to the detector; the detector comprising a pixelated detector.

11. The imaging system of claim 9, wherein two pulses in the double pulsed x-ray source are separated by between 25 µs and 100 µs.

12. The imaging system of claim 9, wherein the scintillator comprises a micro-columnar, low afterglow scintillator; and the micro-columnar, low afterglow scintillator comprises a CsI:Tl, Sm co-doped film.

13. The imaging system of claim 9, wherein the scintillator comprises $Gd_2O_2S(Pr)$.

14. The imaging system of claim 9, wherein the detector comprises a pixelated detector.

15. A method for measurements of a flowing fluid, the method comprising:

illuminating a section of fluid flow with at least one double pulsed x-ray source, where two pulses in the double pulsed x-ray source are separated by between 25 µs and 100 µs;

receiving x-rays from the double pulsed x-ray source after illuminating and propagating through the flowing fluid at one or more scintillators; and providing an output of the one or more scintillators to one or more detectors;

an output from the one or more detectors being used to obtain preselected characteristics of the flowing fluid.

16. The method of claim 15, wherein the flowing fluid comprises blood with particle tracers; the one or more scintillators comprising one scintillator; the one or more detectors comprising one detector; where-in the one detector comprises a pixelated detector; and wherein a characteristic of the flowing fluid comprises blood velocity.

17. The method of claim 15, wherein the flowing fluid comprises fragments from an explosion.

18. The method of claim 17, wherein the at least one double pulsed x-ray source comprises two double pulsed x-ray sources; the one or more scintillators comprising two scintillators; the one or more detectors comprising two detectors; and wherein a characteristic of the flowing fluid comprises velocity of fragments.

* * * * *